United States Patent
Jin et al.

(10) Patent No.: US 9,958,459 B2
(45) Date of Patent: May 1, 2018

(54) APPLICATION OF N-TERMINOMICS TO NETOSIS IN INFLAMMATION

(71) Applicant: Bayer HealthCare LLC, Whippany, NJ (US)

(72) Inventors: Ye Jin, Danville, CA (US); Terry Hermiston, Mill Valley, CA (US); John Murphy, Boston, MA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days. days.

(21) Appl. No.: 14/771,322

(22) PCT Filed: Mar. 14, 2014

(86) PCT No.: PCT/US2014/029040
§ 371 (c)(1),
(2) Date: Aug. 28, 2015

(87) PCT Pub. No.: WO2014/144572
PCT Pub. Date: Sep. 18, 2014

(65) Prior Publication Data
US 2016/0011209 A1 Jan. 14, 2016

Related U.S. Application Data

(60) Provisional application No. 61/799,658, filed on Mar. 15, 2013.

(51) Int. Cl.
*G01N 33/68* (2006.01)
*G01N 33/569* (2006.01)

(52) U.S. Cl.
CPC ... *G01N 33/6893* (2013.01); *G01N 33/56972* (2013.01); *G01N 2333/964* (2013.01); *G01N 2800/065* (2013.01); *G01N 2800/085* (2013.01); *G01N 2800/102* (2013.01); *G01N 2800/104* (2013.01); *G01N 2800/226* (2013.01); *G01N 2800/26* (2013.01); *G01N 2800/368* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 8,569,275 B2 * | 10/2013 | Frincke | C07J 13/005 514/172 |
| 2003/0104479 A1 | 6/2003 | Bright et al. | |
| 2008/0213404 A1 * | 9/2008 | Johnson | A61K 31/00 424/725 |
| 2008/0213800 A1 | 9/2008 | Yamada et al. | |
| 2009/0298078 A1 | 12/2009 | Margraf | |
| 2011/0082155 A1 | 4/2011 | Murugan et al. | |
| 2012/0135443 A1 | 5/2012 | Schultz et al. | |

FOREIGN PATENT DOCUMENTS

WO 2010022281 A1 2/2010

OTHER PUBLICATIONS

Pouyade et al. also measure the serum NE from horse (Veterinary immunology and immunopathology (2010),vol. 135, pp. 181-187).*
Matsuse et al. (Respiratory medicine, (2007), 101(7), 1521-1528).*
Korkmaz et al. (Pharmacol. Review 2010 vol. 62, p. 726-759).*
Miki et al. (World journal of surgery, (2007), 31(3), 522-531).*
Chalkley; et al., "In-depth Analysis of Tandem Mass Spectrometry Data from Disparate Instrument Types", Dec. 2008, vol. 7, 2386-2398.
Choe; et al., "Substrate Profiling of Cysteine Proteases Using a Combinatorial Peptide Library Identifies Functionally Unique Specificities", May 5, 2006, vol. 281 No. 18, 12824-12832.
Choi; et al., "Significance Analysis of Spectral Count Data in Label-free Shotgun Proteomics", Dec. 2008, vol. 7, 2373-2385.
Colaert; et al., "Improved Visualization of Protein Consensus Sequences by iceLogo", Nov. 2009, vol. 6 No. 11, 786-787.
Elias; et al., "Target-decoy search strategy for increased confidence in large-scale protein identifications by mass spectrometry", Feb. 27, 2007, vol. 4 No. 3, 207-214.
Epinette; et al., "A Selective Reversible Azapeptide Inhibitor of Human Neutrophil Proteinase 3 Derived from a High Affinity FRET Substrate", Mar. 15, 2012, vol. 83 No. 6, 788-796.
"Extended European Search Report in corresponding Application No. 14762263.3 dated Jan. 30, 2017".
Groutas; et al., "Neutrophil Elastase Inhibitors", Mar. 1, 2011, vol. 21 No. 3, 339-354.
Guma; et al., "Caspase 1-Independent Activation of Interleukin-1beta in Neutrophil-Predominant Inflammation", Dec. 2009, vol. 60 No. 12, 3642-3650.
Hajjar; et al., "Inspection of the Binding Sites of Proteinase3 for the Design of a Highly Specific Substrate", 2006, vol. 49 No. 4, 1248-1260.
"International Search Report & Written Opinion of International Application No. PCT/US2014/029040 dated Aug. 28, 2014".
Joosten; et al., "Inflammatory Arthritis in Caspase 1 Gene-Deficient Mice: Contribution of Proteinase 3 to Caspase 1-Independent Production of Bioactive Interleukin-1beta", 2009, vol. 60 No. 12, 3651-3662.
Korkmaz; et al., "Influence of Charge Distribution at the Active Site Surface on the Substrate Specificity of Human Neutrophil Protease 3 and Elastase: A Kinetic and Molecular Modeling Analysis", Jan. 19, 2007, vol. 282 No. 3, 1989-1997.
Korkmaz; et al., "Inhibition of Neutrophil Elastase by Alpha1-Protease Inhibitor at the Surface of Human Polymorphonuclear Neutrophils", Sep. 1, 2005, vol. 175 No. 5, 3329-3338.
Lestienne; et al., "Activation of Human Leukocyte Elastase Activity by Excess Substrate, Activation of Human Leukocyte Elastase Activity by Excess Substrate,", Oct. 10, 1980, vol. 255 No. 9, 9289-9294.

(Continued)

*Primary Examiner* — Jacob Cheu
(74) *Attorney, Agent, or Firm* — Bayer Healthcare LLC

(57) ABSTRACT

Provided herein are protein biomarkers for NETosis related diseases, including proteases. Also provided are substrate sequences of such proteases and uses thereof.

11 Claims, 9 Drawing Sheets

(56) References Cited

OTHER PUBLICATIONS

Liu; et al., "A Model for Random Sampling and Estimation of Relative Protein Abundance in Shotgun Proteomics", Jul. 15, 2004, vol. 76 No. 14, 4193-4201.
Mantovani; et al., "Neutrophils in the Activation and Regulation of Innate and Adaptive Immunity", Aug. 2011, vol. 11 No. 8, 519-531.
Meyer-Hoffert; et al., "Neutrophil Serine Proteases: Mediators of Innate Immune Responses", 2011, vol. 18, 19-24.
O'Donoghue; et al., "Global Substrate Profiling of Proteases in Human Neutrophil Extracellular Traps Reveals Consensus Motif Predominantly Contributed by Elastase", Sep. 20, 2013, vol. 8 Issue 9, 1-12.
Perera; et al., "NSP4, an Elastase-Related Protease in Human Neutrophils with Arginine Specificity", Apr. 17, 2012, vol. 109 No. 16, 6229-6234.
Pham; Christine T. N., "Neutrophil Serine Proteases: Specific Regulators of Inflamation", 2006, vol. 6 No. 7, 541-550.
Robertson; et al., "Expression and Alternative Processing of IL-18 in Human Neutrophils", Mar. 2006, vol. 36 No. 3, 772-731.
Salvesen; et al., "Zymogen Activation Specificity and Genomic Structures of Human Neutrophil Elastase and Cathepsin G Reveal a New Branch of the Chymotrypsinogen Superfamily of Serine Proteinases", 1991, vol. 50, 665-671.
Urban; et al., "Neutrophil Extracellular Traps Contain Calprotectin, a Cytosolic Protein Complex Involved in Host Defense against Candida albicans", Oct. 30, 2009, vol. 5 No. 10, 1-18.

\* cited by examiner

Figure 5

| Elastase cleavage site (<60 min) | | | | | | | | |
|---|---|---|---|---|---|---|---|---|
| | P4 | P3 | P2 | P1 | P1' | P2' | P3' | P4' |
| ATGGYHPN | A | T | G | G | Y | H | P | N |
| FVKISTTH | F | V | K | I | S | T | T | H |
| IDWHHXXX | I | D | W | H | H | X | X | X |
| MDSIRHQG | M | D | S | I | R | H | Q | G |
| PAKVWSTY | P | A | K | V | W | S | T | Y |
| QRRGMXXX | Q | R | R | G | M | X | X | X |
| XXPHWQRV | X | X | P | H | W | Q | R | V |
| YRMIRQEX | Y | R | M | I | R | Q | E | X |
| EQFTNMYX | E | Q | F | T | N | M | Y | X |
| GQMIRWHF | G | Q | M | I | R | W | H | F |
| ISTTHWXX | I | S | T | T | H | W | X | X |
| KYPIMAXX | K | Y | P | I | M | A | X | X |
| MQTTQMXX | M | Q | T | T | Q | M | X | X |
| NQIWFDY | N | Q | I | I | W | F | D | Y |
| PHMIWAKP | P | H | M | I | W | A | K | P |
| QINQKHXX | Q | I | N | Q | K | H | X | X |
| RLNTPXXX | R | L | N | T | P | X | X | X |
| RMHVQLGG | R | M | H | V | Q | L | G | G |
| SETIAHFH | S | E | T | I | A | H | F | H |
| YDPVSLXX | Y | D | P | V | S | L | X | X |
| YLAIQAVX | Y | L | A | I | Q | A | V | X |

Elastase only
Elastase/Cathepsin G
Elastase/proteinase 3
Elastase/Cathepsin G/proteinase 3
proteinase 3 only
Cathepsin G and proteinase 3
cathepsin G only cleavage always in the middle between P1 and P1'

Figure 6

| Proteinase 3 cleavage site (within 60 min) | | | | | | | |
|---|---|---|---|---|---|---|---|
| <60 min | P4 | P3 | P2 | P1 | P1' | P2' | P3' | P4' |
| EPNGWXXX | E | P | N | G | W | X | X | X |
| GRDTMFIX | G | R | D | T | M | F | I | X |
| NFLRGPXX | N | F | L | R | G | P | X | X |
| YRMIRQEX | Y | R | M | I | R | Q | E | X |
| AHWVGIXX | A | H | W | V | G | I | X | X |
| AIGARSDX | A | I | G | A | R | S | D | X |
| EQFTNMYX | E | Q | F | T | N | M | Y | X |
| KISTTHWX | K | I | S | T | T | H | W | X |
| MIWAKPGX | M | I | W | A | K | P | G | X |
| MVLTKAAP | M | V | L | T | K | A | A | P |
| TVYADSSE | T | V | Y | A | D | S | S | E |
| XXGPKLTY | X | X | G | P | K | L | T | Y |
| XXXMPEEV | X | X | X | M | P | E | E | V |
| NFLRGPXX | N | F | L | R | G | P | X | X |

| | |
|---|---|
| | Elastase only |
| | Elastase/Cathepsin G |
| | Elastase/proteinase 3 |
| | Elastase/Cathepsin G/proteinase 3 |
| | proteinase 3 only |
| | Cathepsin G and proteinase 3 |
| | cathepsin G only | cleavage always in the middle between P1 and P1'

Figure 7

| Sequence | P6 | P5 | P4 | P3 | P2 | P1 | P1' |
|---|---|---|---|---|---|---|---|
| ANFLRGPX | A | N | F | L | R | G | P | X |
| AQYMMGQX | A | Q | Y | M | M | G | Q | X |
| AVMFMSKX | A | V | M | F | M | S | K | X |
| DHAYLYXX | D | H | A | Y | L | Y | X | X |
| EQTHNYRP | E | Q | T | H | N | Y | R | P |
| ERLFFWAX | E | R | L | F | F | W | A | X |
| ETVYADSS | E | T | V | Y | A | D | S | S |
| GHTFQESM | G | H | T | F | Q | E | S | M |
| GMSFMMXX | G | M | S | F | M | M | X | X |
| HAWFSVII | H | A | W | F | S | V | I | I |
| HEIYGDPX | H | E | I | Y | G | D | P | X |
| IAHFHGID | I | A | H | F | H | G | I | D |
| IFYLNGDX | I | F | Y | L | N | G | D | X |
| KERLFWAX | K | E | R | L | F | F | W | A |
| KLTYDFWI | K | L | T | Y | D | F | W | I |
| KVNFQQHI | K | V | N | F | Q | Q | H | I |
| NMLKDDMG | N | M | L | K | D | D | M | G |
| PDFYLGRS | P | D | F | Y | L | G | R | S |
| RSAFAEMW | R | S | A | F | A | E | M | W |
| RWHFSENX | R | W | H | F | S | E | N | X |
| SEQFTNMY | S | E | Q | F | T | N | M | Y |
| TARWNDVD | T | A | R | W | N | D | V | D |
| TWMKIFNT | T | W | M | K | I | F | N | T |
| VIFFRLNT | V | I | F | F | R | L | N | T |
| VLLRPXXX | V | L | L | R | P | X | X | X |
| WDESNGAX | W | D | E | S | N | G | A | X |
| WNMLKDDM | W | N | M | L | K | D | D | M |
| WSTYKSWV | W | S | T | Y | K | S | W | V |
| XMYFKYIW | X | M | Y | F | K | Y | I | W |
| YIWYVQTA | Y | I | W | Y | V | Q | T | A |
| YKRFMAHW | Y | K | R | F | M | A | H | W |
| YTLKGEHX | Y | T | L | K | G | E | H | X |
| AFMKWHEG | A | F | M | K | W | H | E | G |
| ASMRIYIE | A | S | M | R | I | Y | I | E |
| DDLMSEQF | D | D | L | M | S | E | Q | F |
| DTMFIXXX | D | T | M | F | I | X | X | X |
| DWAFRIRS | D | W | A | F | R | I | R | S |
| FIVFLWR | F | I | V | F | L | I | W | R |
| FNMYGYDL | F | N | M | Y | G | Y | D | L |
| GIFYLNGD | G | I | F | Y | L | N | G | D |
| GQMIRWHF | G | Q | M | I | R | W | H | F |
| HIVKWASX | H | I | V | K | W | A | S | X |
| IIWFDYTL | I | I | W | F | D | Y | T | L |
| IVKWASXX | I | V | K | W | A | S | X | X |
| KGKPTRWQ | K | G | K | P | T | R | W | Q |
| KPHDVMGS | K | P | H | D | V | M | G | S |
| KRFMAHWV | K | R | F | M | A | H | W | V |
| KWSYRMXX | K | W | S | Y | R | M | X | X |
| LHPFKVHX | L | H | P | F | K | V | H | X |
| MAFMKWHE | M | A | F | M | K | W | H | E |
| MAHWVGIX | M | A | H | W | V | G | I | X |
| MFVKISTT | M | F | V | K | I | S | T | T |
| MIALYWGR | M | I | A | L | Y | W | G | R |
| MKIFNTXX | M | K | I | F | N | T | X | X |
| PWTMANFL | P | W | T | M | A | N | F | L |
| QGPFWMLX | Q | G | P | F | W | M | L | X |
| QYPMFVKI | Q | Y | P | M | F | V | K | I |
| RLFFWAXX | R | L | F | F | W | A | X | X |
| STYFHDLN | S | T | Y | F | H | D | L | N |
| TKMHAENI | T | K | M | H | A | E | N | I |
| VGKWSYRM | V | G | K | W | S | Y | R | M |
| VLTKAAPV | V | L | T | K | A | A | P | V |
| WLIFVSNA | W | L | I | F | V | S | N | A |
| XXHGTPKF | X | X | H | G | T | P | K | F |
| XXLFNDVN | X | X | L | F | N | D | V | N |
| YNMWSLYR | Y | N | M | W | S | L | Y | R |

Elastase only
Elastase/Cathepsin G
Elastase/proteinase 3
Elastase/Cathepsin G/proteinase 3
proteinase 3 only
Cathepsin G and proteinase 3
cathepsin G only cleavage always in the middle between P1 and P1'

Figure 8

| Netosis1Donor_0060/Donor000 | | Netosis4Donor_0060/Donor002 | | Netosis7Donor_0060/Donor007 | |
|---|---|---|---|---|---|
| ▓▓▓▓▓ | X | ▓▓▓▓▓ | X | ETVYADSS | |
| ▓▓▓▓▓ | X | ▓▓▓▓▓ | X | ▓▓▓▓▓ | X |
| KQRFHPXX | | IVKWASXX | | GKPTRWQR | |
| KYPIMAXX | X | KYPIMAXX | X | ▓▓▓▓▓ | X |
| MDSIRHQG | X | MDSIRHQG | X | KYPIMAXX | X |
| ▓▓▓▓▓ | | NDSWFDY | X/ | MDSIRHQG | X |
| WQRVIFFR | | RFMAHWVG | X/ | MQTTQMXX | |
| ▓▓▓▓▓ | X/ | SLIAKWVG | X/ | NQIIWFDY | X/ |
| ▓▓▓▓▓ | X | SRQAEXXX | | PAKVWSTY | |
| YRMIRQEX | X | TDWWAYXX | | RFMAHWVG | X/ |
| IRSGTXXX | | ▓▓▓▓▓ | X/ | RMHVQLGG | |
| PFKVHXXX | | XXXAQNEA | | RWLIFVSN | |
| XXXPNITR | | XXXEAWMT | | SLIAKWVG | X/ |
| | | ▓▓▓▓▓ | X | WVARGXXX | |
| | | YRMIRQEX | X | ▓▓▓▓▓ | X |
| | | LQHTFXXX | | YRMIRQEX | X |
| | | | | ▓▓▓▓▓ | |
| | | | | VLLRPXXX | |

APPLICATION OF N-TERMINOMICS TO NETOSIS IN INFLAMMATION

PRIORITY CLAIM

The present application claims benefit of priority to U.S. Provisional Application Ser. No. 61/799,658, filed Mar. 15, 2013, the entire contents of which are hereby incorporated by reference.

FIELD

The present application relates to Neutrophil Extracellular Traps, also referred to as NET(s).

BACKGROUND

Neutrophils are the most abundant leukocytes in plasma. They are the first cells recruited to injury sites in response to pathogen invasion, and they act in the first line of innate immune defense. Neutrophils have traditionally been considered effector cells for inflammatory response and acute immunity, functioning through intracellular phagocytosis, and using lytic proteases, reactive oxygen species (ROS) and microbicidal proteins for attack of infective agents. Recent studies have shown that neutrophils also possess immunoregulatory capacity by expressing cytokines, chemokines, Fc receptors and complement components, for signaling with other immune cells, such as dendritic cells, B cells and T cells (Mantovani, Cassatella et al. 2011).

Proteases are important effectors of neutrophils. They not only contribute directly to microbicidal activity but also function in the proteolytic processing of chemokines, cytokines and receptors (Pham 2006; Meyer-Hoffert and Wiedow 2010). This modulatory activity is exemplified by the caspase-independent activation of IL-1β and IL-18 by NE, PR3 and CG (Robertson, Young et al. 2006; Guma, Ronacher et al. 2009; Joosten, Netea et al. 2009) or the conversion of anti-inflammatory progranulin to pro-inflammatory granulin by NE and PR3 (Kenssenbrock, 2008). Furthermore, NE has been shown to couple neutrophil-mediated inflammation with the coagulation pathway by cleaving tissue factor pathway inhibitor on Neutrophil Extracellular Traps (NETs).

NETs are released by stimulated neutrophils in a specific form of cell death called NETosis. NETosis is hypothesized to represent a new mechanism of innate immunity mediated by neutrophils in response to pathogen invasion (Brinkmann, Reichard et al. 2004; Remijsen, Kuijpers et al. 2011). It is characterized by the formation of NETs, networks made of decondensed chromatin and anti-microbial proteins and peptides. NETosis, acting at the first line of innate immune defense, represents a new paradigm of cell death that is distinct from apoptosis and necrosis in many aspects. No nuclear fragmentation or membrane blebbing are observed, and activation is independent of caspase activation, yet it does require NADPH oxidase and MAPK kinase pathways. NETosis also involves activities of NE, myeloperoxidase, and peptidylarginine deiminase 4, an enzyme responsible for histone citrullination and chromatin decondensation (Wang, Li et al. 2009; Papayannopoulos, Metzler et al. 2010). The primary function of NETs is hypothesized to trap and kill pathogens. In addition, it also provides a matrix for high local concentrations of effectors and mediators for the ensuing innate and adaptive immune responses. Previous proteomic studies of NET components identified three major proteases, namely neutrophil NE, CG and PR3 (Urban, Ermert et al. 2009).

In order to characterize NET-associated proteolytic activities in an unbiased manner, proteins trapped in NETs were released and assayed with the Multiplex Substrate Profiling by Mass Spectrometry (MSP-MS) method (O'Donoghue et al., 2012). This method utilizes a library of 124 highly diversified peptides in a multiplex assay with tandem liquid chromatography-mass spectrometry for detection of cleavage sites. Using the MSP-MS assay, the contribution of each enzyme in the complex NETosis sample was deconvoluted by comparison with substrate specificity profiles from purified human neutrophil proteases. In addition, the non-prime side substrate specificity of NE, CG, PR3 and NSP4 was investigated using a tetrapeptide fluorescent substrate library. Reported here is the first complete study, to the inventors' knowledge, that compares the extended substrate specificity of NE, PR3, CG and NSP4 in parallel under identical conditions. Through the analysis of NET-associated protease mixtures from three independent healthy donors, the major activity could be attributed to NE. Immunodepletion of NE activity revealed contributing activity from PR3 and to a lesser extent CG, as well as a trace of NSP4 activity. Identifying the substrate specificity and the contribution of each NET-associated protease to overall NET-associated activity could lead to the development of improved therapeutic intervention for pathological NETosis in acute and chronic immune diseases.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5 shows Elastase cleavage sites and those it shares with Cathepsin G and Proteinase 3.

FIG. 6 shows Proteinase 3 cleavage sites and those it shares with Elastase and Cathepsin G.

FIG. 7 shows Cathepsin G cleavage sites and those it shares with Elastase and Proteinase 3.

FIG. 8 shows protease cleavage sites from NETosis donors.

SUMMARY

Figure 1:
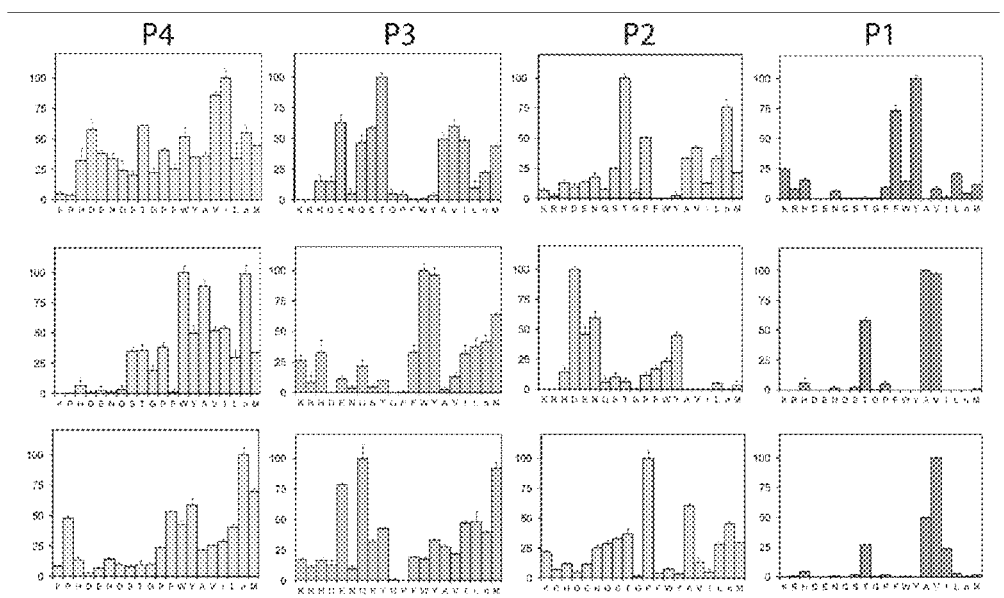
FIG. 1 depicts graphs showing the comparison of the non-prime side specificity of Neutrophil Serine Proteases (top row: Cathepsin G (100 nM), middle row: Proteinase 3 (50 nM), bottom row: Elastase (50 nM)).

Provided herein are protein biomarkers for NETosis related diseases. In some embodiments, such biomarkers are proteases, including for example neutrophil elastase (NE), cathepsin G (CG), proteinase 3 (PR3) and neutrophil secreted protein 4 (NSP4).

Also provided are substrate sequences for which neutrophil elastase (NE), cathepsin G (CG), proteinase 3 (PR3) and neutrophil secreted protein 4 (NSP4) recognize and/or cleave.

In some embodiments, the substrate sequences can be used to develop probes or inhibitors of such proteases. Further, such substrate sequences can be used to develop cleavage sites in polypeptides where cleavage is desired in a NETosis related disease.

Thus, there is provided a method for identifying a subject having a NETosis-related inflammatory condition, wherein NETosis is Neutrophil cell death forming Extracellular Traps, comprising (a) obtaining information on NET-associated protease content from a sample from the subject; (b) comparing the level of NET-associated protease content with that of a comparable sample from a healthy subject, and (c) identifying the subject as having a NETosis-related inflammatory condition when the NET-associated protease content of the sample is greater than that of the comparable sample from the healthy subject.

The sample may be a blood sample. The protease may be selected from the group consisting of neutrophil elastase (NE), cathepsin G (CG), proteinase 3 (PR3), and neutrophil secreted protein 4 (NSP4). The method may further comprise treating the NETosis-related inflammatory condition, such as infection, systemic lupus erythematosus, rheumatoid arthritis, cystic fibrosis, deep vein thrombosis, pre-eclampsia, periodontitis, appendicitis, tuberculosis, and Crohn's disease. Treating may comprise administering to the subject a protease inhibitor. The protease inhibitor may inhibit cleavage of peptide substrate comprising a sequence set forth in FIGS. 4-9. Treating may also comprise administering to the subject a steroid or non-steroidal anti-inflammatory drug, or an antibiotic. The subject may be a human or a non-human mammal.

The method may also comprise obtaining information comprises obtaining a sample from the subject, such as by performing protease content assessment on the sample. The assessment may be by enzyme-linked immunosorbent assay (ELISA), mass spectrometry, chromatography, electrophoresis, radioimmunoassay, flow cytometry, fluorescence activated cell sorting (FACS), or western blotting. The protease content difference between the sample and the comparable sample is +10%, +20%, +25%, +30%, +40%, +50%, +75% or +100%.

It is contemplated that any method or composition described herein can be implemented with respect to any other method or composition described herein. These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

DETAILED DESCRIPTION

It is to be understood that this disclosure is not limited to the particular methodology, protocols, cell lines, animal species or genera, constructs, and reagents described and as such may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a," "and," and "the" include plural reference unless the context clearly dictates otherwise. Thus, for example, reference to "a protease" is a reference to one or more proteases and includes equivalents thereof known to those skilled in the art, and so forth.

As used herein, the term "about" refers to +/−10% of the unit value provided. As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term substantially is therefore used herein to capture the potential lack of completeness inherent in many biological and chemical phenomena.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are hereby incorporated herein by reference for the purpose of describing and disclosing, for example, the constructs and methodologies that are described in the publications which might be used in connection with the presently described embodiments. The publications discussed above and throughout the text are provided solely for their disclosure prior to the filing date of the present application. Nothing herein is to be construed as an admission that the inventors are not entitled to antedate such disclosure by virtue of prior invention.

Serine proteases are important effectors of neutrophil-mediated immunity, which functions at the front line of innate immune response. Neutrophil serine proteases function directly by degrading pathogenic virulent factors and indirectly via processing of their substrates, including cytokines, chemokines and receptors. Proteases also are predicted to be important effectors in NETosis, a novel form of neutrophil cell death. NETosis is hypothesized to be an extracellular defense mechanism utilized by neutrophils to ensnare and kill invading pathogen. These Neutrophil Extracellular Traps (NETs) consist of a host of antimicrobial molecules embedded in a web of extracellular DNA.

Here, reported is the global profiling of NET-associated proteases using unbiased peptide libraries as substrates as shown in FIGS. 5-9. In these peptide-based assays, neutrophil elastase (NE), cathepsin G (CG), proteinase 3 (PR3) and neutrophil secreted protein 4 (NSP4) had overlapping yet distinct endopeptidase activities and often cleaved at unique sites within the same peptide substrate. The dominant proteolytic activity in NETs was attributed to NE, however cleavage sites corresponding to CG and PR3 activity were evident. When NE was immunodepleted, the remaining activity was attributed to CG and to a lesser extent PR3 and NSP4. Thus, blocking NE activity would abrogate the major protease activity associated with NETs. In addition, the newly identified substrate specificity signatures can be used to design more specific probes and inhibitors that target NET-associated proteases.

It was determined that the substrate specificity of four neutrophil serine proteases, NE, PR3, CG and NSP4, using two distinct yet complementary peptide-based substrate libraries, namely PS-SCL and MSP-MS. It was observed that the preferred and non-preferred amino acids in the P1 position correlated strongly between each method while NE and PR3 had strong correlation at multiple sites. CG is likely to be an example of a protease that is incompletely profiled by the PS-SCL method, despite the approximately 100-fold greater sequence diversity in the PS-SCL versus MSP-MS libraries. By design, the activity of CG may require P2' occupancy or it may be adversely affected by the fluorescent ACC group in P1'.

Previously, PICS has been utilized to generate extended substrate specificity profiles of NE, CG and NSP4 (Schilling & Overall 2008; Perera 2012) but not PR3. In these studies, proteome derived peptides were used as the substrate library and cleavage by the neutrophil serine proteases was monitored by mass spectrometry. As was observed for the PS-SCL method, the P1 substrate profiles of each enzyme showed very strong correlation with the inventors' MSP-MS data and is therefore likely that most of the substrate selectivity for this class of enzymes occurs at this subsite. In addition, it was determined that the S2' site of NE and CG may be important for substrate recognition as these sites correlate strongly between methods. Fluorescent substrates that are selective for each neutrophil serine protease can be developed. These substrates were designed from sequences derived from the reactive loop of a serpin, crystallographic data or positional scanning (Polanowska, 1998; Hajjar, J Med Chem 2006; Wysocka 2012). Accordingly, selective substrates identified can be utilized to develop substrates that have greater selectivity at both the prime and non-prime side of the scissile bond.

Fresh neutrophils isolated from human serum were treated with PMA to induce NETosis and proteins embedded in the NETs were subsequently released following treatment with a nuclease. Proteomic analysis was used to identify proteins released from the NETs, many of which have been observed in a previous study (Urban, Ermert et al. 2009). Interestingly, NE remained tightly bound to intact DNA and was not found in samples that lacked nuclease treatment. CG was found in all samples independent of treatment regimes while PR3 and NSP4 were never observed. At a functional level, proteolytic activity in the supernatant increased upon release of embedded NET proteins therefore providing a set of human neutrophil preparations for multiplex substrate profiling.

MSP-MS is an ideal technology to profile complex biological samples because unlike the PS-SCL and PICS methods, the substrate population consists of a defined set of peptides and therefore cleavage sites can be directly linked to a specific enzyme. The reproducibility of both the sample preparation and the protease assay was evident as most of the substrates cleaved in three independent donor samples were identical. This allowed the generation of a substrate signature for all common cleavage sites. This signature has similar features to the NE signature, particularly at the P4 to P2' subsites and therefore NE was likely to be the dominant proteolytic activity in the neutrophil preparations. This dominance was subsequently confirmed when immunoprecipitation of the enzyme resulted in a loss of NE-specific cleavage sites and alteration of the overall substrate signature. The remaining activity was likely to be the product of CG and to a lesser extent PR3, NSP4 and other as yet unidentified neutrophil proteases.

The advantage of a global and unbiased substrate profiling assay is that activity of all proteases can be monitored simultaneously. In addition, the dominant protease can be readily identified. In this study, it is evident that targeting of NE on NETs would minimize any adverse effects of unregulated proteolysis associated with NETosis. The selective cleavage sequences of the neutrophil serine proteases identified in this study will be valuable for designing substrates, inhibitors and protease-activatable prodrugs (Choi 2012; PMID 22400063). In addition, the substrate signature of NETs-associated protease activity can be monitored as a biomarker for inflammatory diseases driven by the neutrophil NETosis.

EXAMPLES

It will be apparent to those skilled in the art that the examples and embodiments described herein are by way of illustration and not of limitation, and that other examples may be used without departing from the spirit and scope of specific embodiments, as set forth in the claims.

Example 1. Materials and Methods

Proteolytic Activity Using Combinatorial Fluorogenic Substrate Libraries

Non-prime side sequence specificity, as the N-terminal sequence relative to the scissile bond is termed in protease nomenclature, was assayed for proteases using combinatorial fluorogenic substrate libraries (Harris, 2000). This fluorescent peptide library is amenable for detailed profiling of purified serine proteases and distinguishes between subsite preferences in closely related enzymes. Human NE (50 nM), CG (100 nM), PR3 (50 nM) (Athens Research & Technology, Cat#16-14-051200; Cat#16-14-030107; Cat#16-14-161820) and NSP4 (100 nM) were assayed with this fluorogenic library in Dulbecco's-PBS containing 0.01% Tween-20. Amino acid preferences at each position can be determined by direct comparison of activity, in units of picomolar of fluorophore released per second.

Peptide Cleavage Site Identification by Multiplex Substrate Profiling-Mass Spectrometry Human NE (1 nM), CG (5 nM), PR3 (2 nM) and NSP4 (25 nM) were profiled using the MSP-MS assay as described by O'Donoghue et al. 2012. In addition, proteolytic activities in three PMA-induced and MNase-treated donor NET samples were determined using the MSP-MS assay. Control samples lacked PMA or MNase treatment and consisted of an equal mixture of total protein from each donor. All assays contained 0.4 µg/mL of donor protein and 500 nM of each peptide in a total reaction volume of 900 µl. Aliquots were removed after 15, 60, 240, and 1200 minutes and quenched with concentrated formic acid to a final pH of 2.5. Samples were desalted and analyzed by LC-MSMS peptide sequencing.

For LC-MS/MS, an LTQ-FT mass spectrometer (Thermo) equipped with a 10,000 psi system nanoACUITY (Waters) UPLC instrument was used for reversed phase chromatography with a C18 column (BEH130, 1.7 µm bead size, 100 µm×100 mm) The LC was operated at 600 nL/min flow rate, and peptides were separated using a linear gradient over 42 min from 2% B to 30% B, with solvent A: 0.1% formic acid in water and solvent B: 0.1% formic acid in 70% acetonitrile. Survey scans were recorded over 350-1800 m/z range, and MS/MS was performed with CID fragmentation on the six most intense precursor ions. Mass spectrometry peak lists were generated using in-house software called PAVA, and data were searched using Protein Prospector software v. 5.10.0 (Chalkley, Baker et al. 2008). Data was searched against a database containing the sequences of the 124 14-mer synthetic peptides, concatenated with 4 different copies of randomized sequences for the same 124 entries to create a final database of 620 sequences for estimation of false discovery rate (O'Donoghue et al, 2012). For database searching, peptide sequences were matched with no enzyme specificity requirement, and variable modifications including oxidation of Trp, Pro and Phe, and N-terminal pyroGlu from Gln. Protein Prospector score thresholds were selected to be minimum protein score of 20, minimum peptide score of 15, and maximum expectation values of 0.1 for "protein" and 0.05 for peptide matches, and resulted in a peptide false discovery rate of 0.2%. Cleavage site data was extracted from Protein Prospector using an in house script called "MSP extractor" software (O'Donoghue et al, 2012). The earliest time interval that ≥2.5% (n=41) of all possible bonds in the library (n=1612) were cleaved was chosen to compare enzymes specificity. NE, PR3 and CG reached this value at 240, 1200 and 60 minutes respectively while NSP4 cleaved only 1.2% (n=19) of peptide bonds over the course of the assay. For comparison of substrate specificity, an iceLogo software was used to generate substrate specificity logos for amino acids at ±4 positions adjacent to the identified cleavage sites with a P value statistic of ≤0.05 (Colaert, Helsens et al. 2009).

Isolation of Neutrophils from Healthy Donors

Human neutrophil cells were isolated by a two-step purification protocol using Red Blood Cell (RBC) sedimentation followed by removal of monocytes using Ficoll density gradient centrifugation. Briefly, 50 ml of fresh human whole blood was collected in a collection tube containing heparin. Blood was mixed with HetaSep (STEM cell, Cat#07906) at the ratio (5:1) to precipitate RBCs and platelets. Supernatants with enriched leukocytes and monocytes were layered on top of Ficoll-PAQUE PLUS (GE Healthcare, Cat#17-1440-03). After Ficoll gradient centrifugation, neutrophils were separated from monocytes in the supernatant and pelleted. Contaminating RBCs were further removed by repeated cell lysis using RBC lysis buffer (Miltenyi Biotec, Cat#130-094-183). By this method, 50-100 million neutrophils were isolated to greater than 98% neutrophil purity, as confirmed by flow cytometry using CD66b antibodies (BD Pharmamingen, Cat#555724).

NETosis Induction and NET Preparation

Purified neutrophils were washed five times to remove plasma proteins, then seeded at a density of $1.7 \times 10^6$ cells/ml in RPMI 1640 media supplemented with glutamine in a 10 mm culture plate. NETosis was induced in vitro by stimulating neutrophils with 50 nM phorbol-12-myristate-13-acetate (PMA, Sigma P8139) at 37° C. in a 5% $CO_2$ incubator. After induction for 3 hours, media was removed and plates were washed gently with warm media three times. This induction time was selected as the optimal time required for maximum protein release from NETs post-PMA treatment. NETs were then digested by Micrococcal Nuclease (MNase) (20 U/ml) (Thermo Scientific, P#88216) for 10-40 minutes to disassemble NETs into media. The supernatant was subsequently centrifuged to remove cells and cellular debris. Supernatants from PMA-untreated neutrophils and PMA-treated neutrophils but without MNase digestion were prepared as negative controls. A fraction of each sample was treated with protease inhibitor cocktail to preserve the sample for proteomic analysis, whereas the remainder of the sample for protease activity screening was not treated with protease inhibitors. The progression of NETosis was monitored by measuring cell-free DNA using Sytox Orange (Life Technologies, S11368). DNA was quantified by relative fluorescence measurement with a SpectraMax M2 fluorometer (Molecular Devices) at a filter setting of 544 nm (ex)/590 nm (em), calibrated by standard curve with DNA standard of known concentration. NETosis was also quantified by measuring NE activity using the EnzChek® elastase Assay Kit (Invitrogen, Cat#12056). Finally NETosis was visually examined by confocal immunofluorescent microscopy. Neutrophils ($5 \times 10^5$ cells/ml) were seeded on poly-L-lysine coated cover slips and treated with or without 50 nM PMA. At different time points post-NETosis induction, cells were fixed with 4% paraformaldehyde, then permeablized and blocked with 10% FBS in phosphate buffered saline (PBS) with 0.05% TritonX-100. For histone staining, coverslips were incubated with a mouse anti-human core histone antibody (Millipore, Anti-histone Clone H11-4, MAB3422) followed a Tetramethyl Rhodamine Isothiocyanate (TRITC)-conjugated secondary antibody (Invitrogen Cat# T2762). DNA was counterstained with Hoechst 33342 (AnaSpec Inc, Cat#83218). Coverslips were mounted onto glass slides using Prolong Gold mounting media (Invitrogen Cat# P36930) before acquisition.

Depletion of Elastase from NET Supernatants

MNase preparations of NET samples were secondarily digested with DNase (100 U/ml) for 10 minutes at 37° to fully release NET-associated proteins. NET supernatants were then mixed with Pierce G/A magnetic beads (Thermo Scientific, Cat#88802) coated with elastase antibodies (Sigma, Cat# PAI-74132) at 4° C. for 1 hour. After incubation, the supernatants were separated from beads on a DYNAL-magnet bead separation rack (Invitrogen Cat#123-21D). Depletion of the protease was confirmed using the EnzChek® elastase assay.

NET Protein Identification by Mass Spectrometry

Protein identification in NET-induced samples was performed using peptide sequencing by mass spectrometry as previously reported (O'Donoghue et al, 2012). NET samples were prepared as described above from three donors with the following combinations: +PMA/+MNase, +PMA/−MNase, and −PMA/+MNase treatment. The +PMA/+MNase treated samples were assayed individually for each donor, while the +PMA/−MNase, and −PMA/+MNase control samples were prepared as pooled mass-matched samples from the three donors. NET protein concentrations ranged from 25-40 μg/ml in PBS, therefore a slightly modified in solution trypsin digestion protocol was applied, as follows. Samples were brought to a standardized concentration of 30 μg/ml with 100 mM ammonium bicarbonate buffer (~20 μg in a total volume of 700 μl) to which was added solid urea to 4M final. Sample was reduced with 10 mM DTT incubation for 10 min at 56° C., then alkylated with 12 mM iodoacetamide (45 min, dark, 21° C.), and then quenched with 5 mM additional DTT. The final volume was adjusted to 1.4 ml with additional 100 mM ammonium bicarbonate, bringing urea concentration to 2M. Trypsin (sequencing grade, Promega) was added at 1:50 trypsin:total protein for digestion overnight at 37° C. The sample was then acidified with formic acid to pH 2-3 and desalted using C18 OMIX tips (Varian). Each sample was assayed with two technical replicate LC-MS/MS analyses using an LTQ-Orbitrap (Thermo) mass spectrometer operated under identical separation and analysis conditions as the LTQ-FT system described above.

Database searches were performed against the *H. sapiens* UniProt database (downloaded Mar. 21, 2012), containing 62,611 entries. For estimation of false discovery rate, this database was concatenated with a fully randomized set of sequence entries (Elias and Gygi 2007). Data were searched with mass tolerances of 20 ppm for parent and 0.8 Da for fragment ions. Peptide sequences were matched as tryptic peptides with no missed cleavages, and carbamidomethylated cysteines as a fixed modification. Variable modifications included oxidation of Met, N-terminal pyroGlu from Gln, loss of Met and N-terminal acetylation. Protein Prospector score parameters were minimum protein score of 22, minimum peptide score of 15, and maximum expectation values of 0.01 for protein and 0.001 for peptide matches, resulting in a protein false discovery rate of 1.1%. Protein identification results are reported with unique peptide count, peptide count as an approximation of protein abundance, percent sequence coverage and an expectation value for the probability of the protein identification (Choi, Fermin et al. 2008) (Liu, Sadygov et al. 2004). Proteins were required to have been identified with at least two unique peptides in one of the three conditions tested (+PMA/+MNase, +PMA/−MNase, and −PMA/+MNase) to be reported.

Example 2. Substrate Profiling of Neutrophil Serine Proteases by PS-SCL and MSP-MS To date, the substrate specificity of more than 80 endoproteases have been profiled using the PS-SCL assay (PMID 10869434) while the recently developed MSP-MS assay has profiled >30 proteases to date, that include endo and exo-acting proteases (O'Donoghue et al, 2012). In order to obtain an unbiased and comprehensive substrate profile of NE, CG, PR3 and NSP4, the inventors assayed each enzyme using PS-SCL and MSP-MS method under identical buffer conditions. The PS-SCL library uses a 7-amino-4-carbamoylmethylcoumarin (ACC) group linked to the carboxy terminus of tetrapeptide sequences. The library can be used to determine the nonprime-side (N-terminal to the scissile bond) substrate specificity and is particularly informative to differentiate proteases with high homology (Choe, Leonetti et al. 2006). In the inventors' studies using the PS-SCL method, both NE and PR3 favor valine and alanine and to a lesser extent, threonine at the P1 site (FIG. 1). NE also can accommodate isoleucine at this position while PR3 does not. In contrast, CG has low tolerance for these amino acids and prefers tyrosine and phenylalanine at its P1 site while NSP4 strongly favors arginine. NE and PR3 are readily distinguishable by the P2 specificity as NE prefers proline and alanine while PR3 displays a preference for aspartic acid, glutamic acid and asparagine. Interestingly, CG and NSP4 prefer threonine, serine, proline and other small hydrophobic amino acids at P2 although for NSP4 this activity is minor relative to the P1 site specificity for arginine. At P3, NE and CG have a similar specificity profile while PR3 has a distinct preference for bulky residues particularly tryptophan and tyrosine. Finally at P4, NE, CG and NSP4 have broad specificity while PR3 does not tolerate phenylalanine or any charged amino acid at this site.

Figure 2:
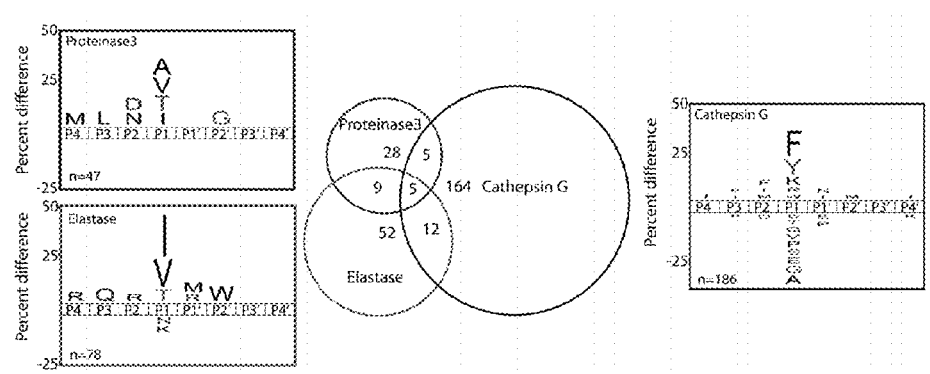
FIG. 2 shows a comparison of the extended substrate specificity of Neutrophil Serine Proteases.

The MSP-MS assay uses a mixture of 124 tetradecapeptides as the substrate library to profile the specificity of proteases. Cleaved peptides at the amino and carboxy side of the scissile bond can be readily identified by peptide sequencing using mass spectrometry. The assay can be quenched at various time intervals to obtain a qualitative assessment of protease cleavage events. All four proteases had significant enrichment of amino acids in the P1 position (FIG. 2), with amino acid preferences that correlated strongly to those observed in the PS-SCL method, scoring ≥0.4 on a scale from −1.0 to 1.0 by Pearson analysis (Table 1). Here, NE favored isoleucine over valine and threonine while PR3 had approximately equal preference for alanine, valine, threonine and isoleucine. CG favored phenylalanine over tyrosine and lysine but disfavored alanine at P1 while NSP4 had a strict preference for arginine. Outside of the P1 subsite, the specificity for each enzyme was derived from different subsites: notably glutamine and leucine were preferred at P3 and tryptophan at P2' of NE, glutamic acid and asparagine at P2 of PR3, and norleucine at P2 of CG. Interestingly, while PR3 and NE had strong correlation within the P4-P1 sites that could be compared between these two methods, CG had a weaker correlation (Table 1), potentially due to prime-side specificity (FIG. 2) that is untested by design in the PS-SCL method. The MSP-MS results showed a strong correlation with previously published specificity data for both NE and CG in the P2' site, as well as P1 (Table 1), that was generated using the proteomic identification of protease cleavage sites (PICS) method (Schilling 2008, Perera 2012).

TABLE 1

| | Comparison of substrate specificity from MSP-MS with PS-SCL and PICS | | | | | | | | | | | |
|---|---|---|---|---|---|---|---|---|---|---|---|---|
| | MSP-MS v PS-SCL | | | | MSP-MS v PICS | | | | | | | |
| | P4 | P3 | P2 | P1 | P4 | P3 | P2 | P1 | P1' | P2' | P3' | P4' |
| NE | 0.53 | 0.72 | 0.41 | 0.51 | −0.15 | 0.53 | 0.29 | 0.87 | −0.03 | 0.46 | 0.01 | 0.05 |
| PR3 | 0.62 | 0.25 | 0.84 | 0.77 | −0.23 | 0.21 | 0.03 | 0.81 | 0.34 | 0.65 | 0.11 | 0.14 |
| CG | 0.06 | 0.28 | 0.12 | 0.81 | — | — | — | — | — | — | — | — |
| NSP4 | −0.19 | 0.14 | 0.20 | 0.96 | 0.15 | 0.22 | −0.32 | 0.93 | 0.10 | 0.01 | −0.23 | −0.10 |

Example 3. Induction of NETs with Enriched Protease Activity

Figure 3:
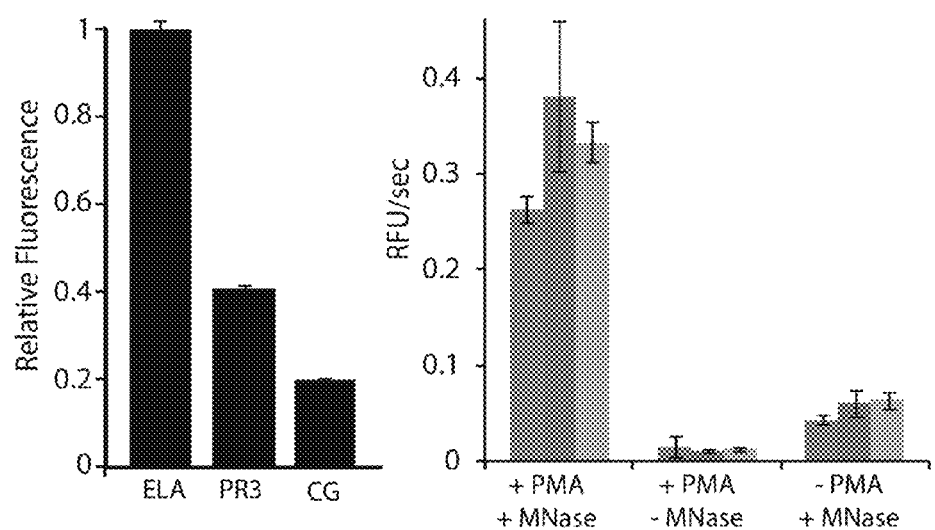
FIG. 3 shows the identification of a fluorescent substrate to simultaneously monitor Elastase (ELA), Proteinase 3 (PR3) and Cathepsin G (CG) cleavage and use of this substrate to determine the total proteolysis in donor neutrophils.

To estimate proteolytic activity in PMA-induced NETosis in neutrophils the inventors screened a set of internally quenched fluorescent peptides and identified a substrate that was readily cleaved by three of the four neutrophil serine proteases. This substrate, K(mca)-PLGKQVEY-K(dnp), was previously used to assay a glutamic acid protease secreted from a fungus (O'Donoghue, 2008). Using this probe, the proteolytic activity released from NETs derived from PMA and MNase treated neutrophils was approximately five-fold greater than control samples that lack PMA treatment, and twenty- to forty-fold greater than control samples that lacked MNase treatment (FIG. 3). The inventors also employed MSP-MS to analyze the same samples and observed 98 cleaved peptide bonds derived from NET-associated proteases. As was evident in the inventors' studies using the fluorescent substrates, there are active proteases present in both PMA only and MNase only treated samples, but these low level cleavages account for only 15-19% of the total cleaved bonds observed after PMA and MNase treatment of neutrophils. Taken together, these studies determined that neutrophils could be induced to form NETs that were enriched with proteolytic activity.

Example 4. Identification of NET Associated Proteins

To identify the full complement of proteins embedded in the NETs, protein preparations from the same NETosis-induced neutrophils described above were subjected to proteomic analysis to evaluate the protein composition of induced versus uninduced NETs (Table 2). Using mass spectrometry, fifty NET-associated proteins were identified in the three conditions (+PMA/+MNase, +PMA/−MNase, and −PMA/+MNase) tested. The NET associated proteins can be grouped into six classes based on their functions and cellular locations: nuclear proteins, actin-associated proteins, enzymes, microcidal peptides and signal transduction. Of these, 21 proteins, mostly among the highest abundance proteins, were previously identified in NETosis induced neutrophils (Urban, Ermert et al. 2009). Only three proteins from the previous study were undetected using the inventors' optimized procedure: proteinase 3, alpha-actinin, and catalase, but these omissions might be explained by the inventors' use of MNase treatment to dissemble NET instead of Dnase treatment such that these 3 proteins might be missed. Twenty-nine (29) proteins were revealed that were previously unidentified in PMA- and MNase-treated neutrophil samples. However only 11 of these proteins were reproducibly identified in all three donors. Among the newly found proteins, the inventors found SH3 domain-binding glutamic acid-rch-like protein 3 (SH3BGRL3) (Q5T123), which are involved in signal transduction pathways of inflammation. NE and the inactive serine protease family member, azurocidin, were found in all three donor samples while CG was only observed in a single donor sample. Surprisingly, while the inventors' enzymatic studies indicated an enrichment of proteolytic activity in PMA- and MNase-treated neutrophils (NETs) relative to the control samples, there was little or no enrichment of proteases in the same samples when analyzed by mass spectrometry-based proteomics. NE was not found in any sample that lacked MNase treatment, indicating that NE is efficiently trapped on intact NETs.

TABLE 2

NET associated proteins identified by LC-MS/MS from three healthy donors

| UniProt Accession# | PMA induced, Mnase treated NETs | | | PMA induced, no nuclease release | | Uninduced, Mnase treated NETs | | Protein MW | Protein Name | Urban et al |
|---|---|---|---|---|---|---|---|---|---|---|
| | Number Unique | Average Peptide Count | Times Observed out of N = 3 | Number Unique | Peptide Count | Number Unique | Peptide Count | | | |
| B4E335 | 43 | 17.33 | 1 | 97 | 173 | 73 | 141 | 39226.3 | Actin, beta | yes |
| P05164 | 99 | 97.33 | 3 | 27 | 43 | 35 | 47 | 83869.4 | Myeloperoxidase | yes |
| A8K9U8 | 71 | 41.67 | 2 | 80 | 128 | 43 | 65 | 78338.9 | Lactoferrin | yes |
| P08246 | 59 | 68.33 | 3 | | | 36 | 64 | 28518.3 | Neutrophil elastase | yes |
| B4DLA9 | 43 | 42.00 | 1 | 14 | 24 | 21 | 47 | 14841.5 | Histone H2B | yes |
| B2R4P9 | 43 | 54.33 | 3 | | | | | 15328 | Histone H3 | yes |
| A3KPC7 | 38 | 39.33 | 2 | | | | | 13906.4 | Histone H2A | yes |
| P20160 | 33 | 32.67 | 3 | 10 | 13 | 12 | 13 | 26885.9 | Azurocidin | yes |
| B2R4R0 | 30 | 51.00 | 3 | 8 | 9 | 20 | 41 | 11367.4 | Histone H4 | yes |
| P35579 | | | | 23 | 30 | | | 226534.2 | Myosin-9 | yes |
| B3KSI4 | 8 | 2.67 | 1 | 8 | 11 | 24 | 31 | 58982.1 | Uncharacterized protein, highly similar to transketolase | yes |
| P06733 | 14 | 7.33 | 3 | | | 20 | 32 | 47169.4 | Alpha-enolase | yes |
| A3R0T8 | 11 | 7.00 | 3 | 18 | 25 | 7 | 12 | 21865.4 | Histone 1, H1e | no |
| B2R4C5 | 17 | 6.33 | 1 | 21 | 23 | 18 | 23 | 16537.2 | Lysozyme | yes |
| P08311 | 15 | 6.00 | 1 | 14 | 20 | 10 | 13 | 28837.5 | Cathepsin G | yes |
| B2R4M6 | 3 | 1.00 | 1 | 14 | 24 | 16 | 28 | 13210.1 | Protein S100-A9 | yes |
| P59665 | 14 | 25.00 | 3 | 16 | 59 | 13 | 37 | 10201.1 | Neutrophil defensin 1 | yes |
| A4UCT1 | 10 | 4.67 | 3 | 11 | 13 | 14 | 20 | 17303.1 | Glyceraldehyde-3-phosphate dehydrogenase (Fragment) | no |
| B2R829 | | | | 20 | 27 | | | 45850.5 | cDNA, FLJ93711, highly similar to Homo sapiens myeloid cell nuclear differentiation antigen (MNDA), mRNA | yes |
| A2A418 | 4 | 1.33 | 2 | 13 | 14 | 13 | 17 | 80641.3 | Gelsolin (Amyloidosis, Finnish type) | |
| C5HZ13 | | | | | | 12 | 21 | 16453 | Charcot-Leyden crystal protein | no |
| B4DE36 | 2 | 1.00 | 2 | | | 8 | 10 | 60186.3 | Glucose-6-phosphate isomerase | no |
| P07737 | 3 | 3.00 | 2 | 3 | 3 | 7 | 10 | 15054.4 | Profilin-1 | no |
| P31146 | 5 | 1.67 | 1 | | | 11 | 22 | 51026.7 | Coronin-1A | no |
| A8K4W6 | | | | 7 | 8 | 9 | 11 | 44615.1 | Phosphoglycerate kinase | no |
| B4DNK4 | | | | 6 | 7 | | | 49898.2 | Pyruvate kinase | no |
| P80723 | | | | 6 | 6 | 3 | 3 | 22693.6 | Brain acid soluble protein 1 | no |

TABLE 2-continued

NET associated proteins identified by LC-MS/MS from three healthy donors

| UniProt Accession# | PMA induced, Mnase treated NETs | | | PMA induced, no nuclease release | | Uninduced, Mnase treated NETs | | Protein MW | Protein Name | Urban et al |
| --- | --- | --- | --- | --- | --- | --- | --- | --- | --- | --- |
| | Number Unique | Average Peptide Count | Observed Times out of N = 3 | Number Unique | Peptide Count | Number Unique | Peptide Count | | | |
| B0YJC4 | | | | | | 10 | 16 | 49653.8 | Vimentin | no |
| B4E112 | | | | 3 | 6 | 4 | 7 | 12459.7 | cDNA FLJ5143S, moderately similar to Cofilin-1 | no |
| A2VCK8 | 4 | 4.00 | 2 | 8 | 25 | 5 | 22 | 5052.7 | Thymosin beta 4, X-linked | no |
| P12724 | | | | 6 | 7 | | | 18385.5 | Eosinophil cationic protein | no |
| P05109 | 5 | 2.67 | 3 | 3 | 5 | 7 | 9 | 10834.6 | Protein S100-A8 | yes |
| A8K220 | | | | 3 | 4 | 4 | 7 | 18012.7 | Peptidyl-prolyl cis-trans isomerase | no |
| A8MX94 | | | | | | 3 | 3 | 19480.7 | Glutathione S-transferase pi 1 | no |
| F2Z393 | 1 | 0.33 | 1 | | | 4 | 4 | 35329.2 | Transaldolase | no |
| B4DJI2 | | | | 4 | 6 | 1 | 2 | 56853.5 | cDNA FLJ53342, highly similar to Granulins | no |
| A8K2Y9 | | | | | | 5 | 6 | 53140.5 | 6-phosphogluconate dehydrogenase, decarboxylating | no |
| P49913 | | | | 4 | 4 | | | 19301.6 | Cathelicidin antimicrobial peptide | no |
| O60234 | 1 | 0.33 | 1 | 3 | 3 | | | 16801.5 | Glia maturation factor gamma | no |
| D6R9A6 | 1 | 0.67 | 1 | 6 | 14 | | | 15403.9 | High mobility group box 2 (Fragment) | no |
| A8K2L4 | | | | 3 | 4 | 1 | 1 | 37247.9 | cDNA FLJ76079, highly similar to *Homo sapiens* lymphocyte-specific protein 1 (LSP1), mRNA | no |
| P80511 | 2 | 1.00 | 1 | | | | | 10575.1 | Protein S100-A12 | yes |
| B3KUI1 | 1 | 1.33 | 3 | 3 | 4 | 3 | 4 | 25043.3 | cDNA FLJ39956 fis, clone SPLEN2024990, highly similar to Plastin-2 | yes |
| B5BU38 | | | | | | 3 | 4 | 38680.6 | Annexin | |
| A7XZE4 | | | | 2 | 3 | 3 | 3 | 33026.2 | Beta tropomyosin isoform | no |
| Q5T123 | 3 | 1.67 | 2 | 2 | 3 | | | 9380.6 | SH3 domain binding glutamic acid-rich protein like 3 | no |
| P05204 | | | | 3 | 8 | 2 | 11 | 9392.7 | Non-histone chromosomal protein HMG-17 | no |
| B0QZK8 | | | | 2 | 2 | | | 13683.9 | Heterochromatin protein 1, binding protein 3 (Fragment) | no |
| B7Z507 | | | | | | 2 | 2 | 71554.8 | cDNA FLJ51036, highly similar to Matrix metalloproteinase-9 (EC3.4.24.35) | no |
| Q68D08 | | | | | | 2 | 2 | 36750.3 | Putative uncharacterized protein DKFZp686B04128 | no |

Example 5. Multiplexed Substrate Profiling of Proteases on NETs

Figure 4:
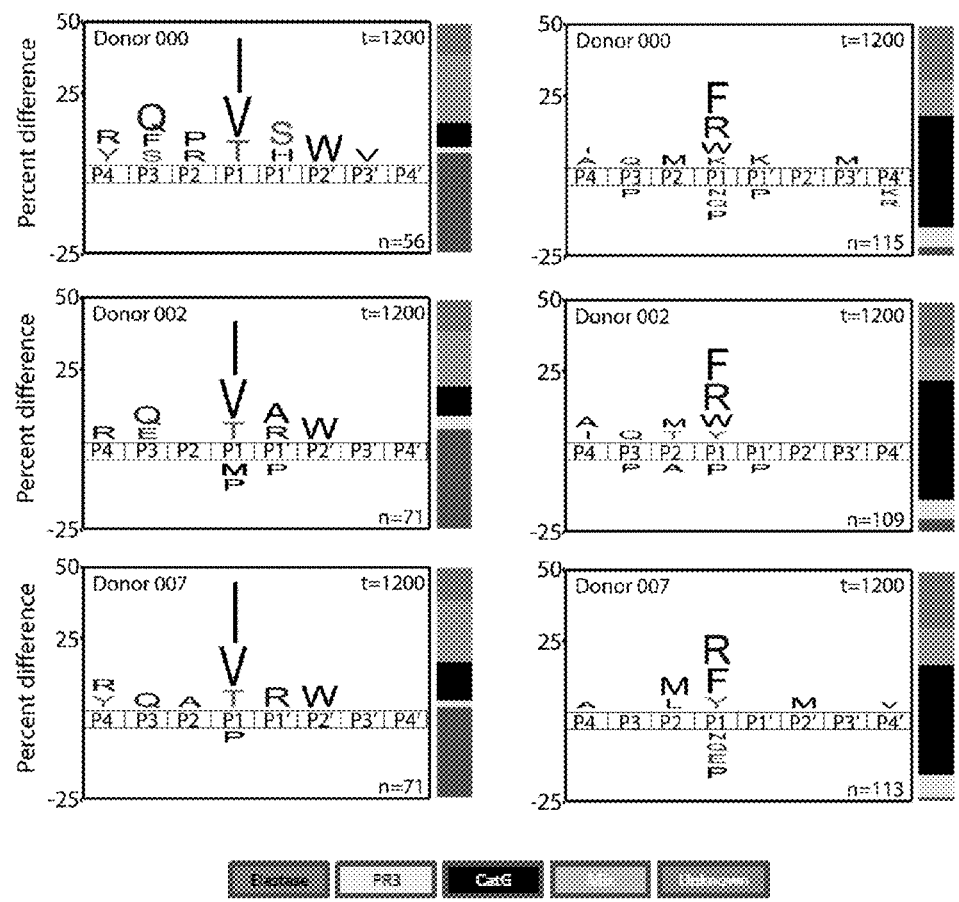
FIG. 4 is a comparison of the proteolytic profile of NETs and immunodepletion of the major activity.

The substrate specificity of NET-associated proteases was assessed using the MSP-MS assay. An advantage of using the MSP-MS assay over the PS-SCL assay for profiling biological samples containing more than one protease, is that peptide substrates can be directly linked to a specific protease. This substrate specificity information of each neutrophil serine protease was applied to the analysis of NETs that are likely to contain a mixture of these enzymes. By MSP-MS, all three donors have similar substrate profiles. To generate a representative "donor signature", the 40 cleavages observed in all three donor samples were aggregated into a single motif that closely resembled NE specificity (FIG. 4). This donor signature was an aggregate of the three major enzyme specificities, with 15, 5, and 1 cleavages uniquely attributable to NE, CG and PR3 respectively (also shown in FIG. 4). The remaining 19 cleavages could not be uniquely assigned, as they were hydrolyzed by more than one neutrophil serine protease.

In order to confirm that NE was the major proteolytic activity in NETs, the inventors selectively removed the enzyme by immunodepletion, and assayed the remaining proteases in the mixture. On this occasion, the inventors were able to increase the total amount of NE-depleted donor protein in the assay by 15-fold, which generated only a 1.7-fold increase in the number of cleavage sites identified over the course of the assay. The 76 shared cleavage sites between three donors were mainly attributable to CG activity (36 unique cleavages), and now revealed proportionately more PR3 activity with 7 unique cleavages. Interestingly, just a single cleavage was likely to be the product of NSP4 activity, and there were now 15 new cleavages that could not be attributed to any of the four enzymes. Thus NE-depletion was able to reveal greater activity for the lower abundance proteases.

Example 6. Substrates of Proteases on NETs

Figure 9:
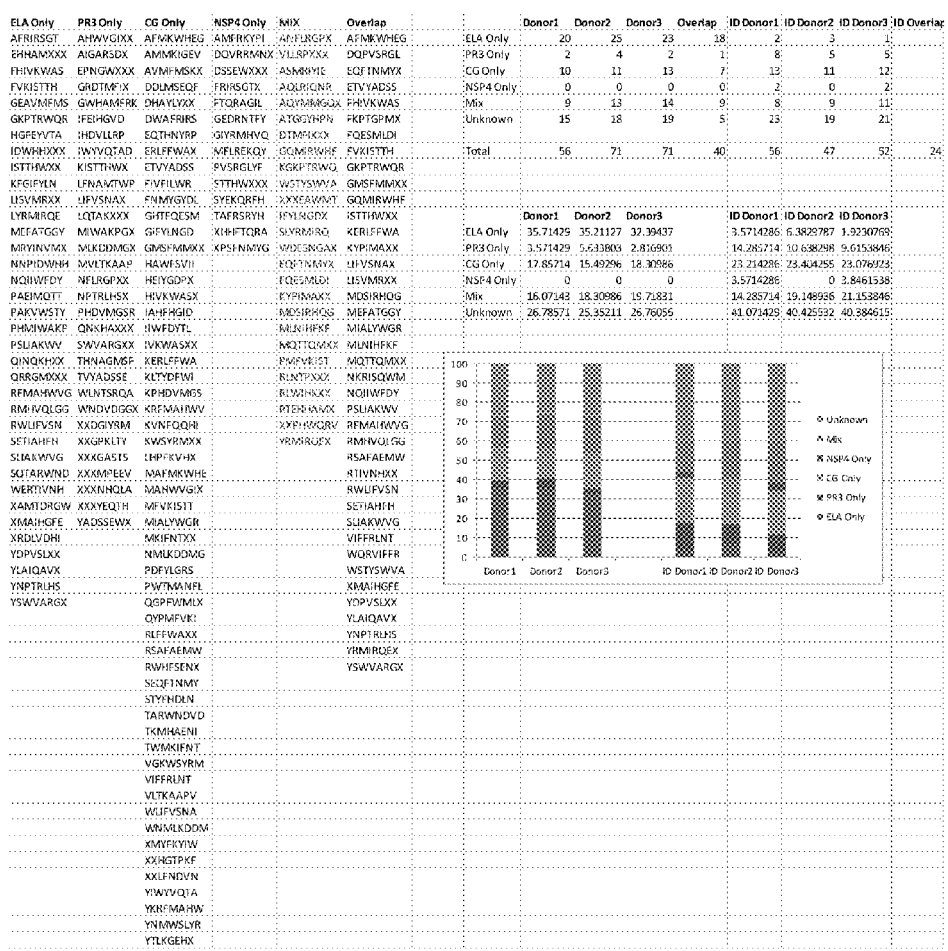
FIG. 9 shows cleavage sites of Elastase, Proteinase 3, Cathepsin G, neutrophil secreted protein 4, and protease cleavage results from NETosis donors.

FIG. 5 shows Elastase cleavage sites and those it shares with Cathepsin G and Proteinase 3. FIG. 6 shows Proteinase 3 cleavage sites and those it shares with Elastase and Cathepsin G. FIG. 7 shows Cathepsin G cleavage sites and those it shares with Elastase and Proteinase 3. FIG. 8 shows protease cleavage sites from NETosis donors. FIG. 9 shows cleavage sites of Elastase, Proteinase 3, Cathepsin G, neutrophil secreted protein 4, and protease cleavage results from NETosis donors.

All publications and patents mentioned in the above specification are incorporated herein by reference. Various modifications and variations of the described methods will be apparent to those skilled in the art without departing from the scope and spirit of the disclosure. Although the invention has been described in connection with specific embodiments, it should be understood that what has been claimed should not be unduly limited to such specific embodiments. Indeed, various modifications of the above-described modes for carrying out specific embodiments which are obvious to those skilled in the art are intended to be within the scope of the following claims. Those skilled in the art will recognize, or be able to ascertain using no more than routine experimentation, many equivalents to the specific embodiments described herein. Such equivalents are intended to be encompassed by the following claims.

The invention claimed is:

1. A method for identifying a subject having a NETosis-related inflammatory condition, wherein NETosis is Neutrophil cell death forming Extracellular Traps, comprising:
   (a) determining information on NET-associated protease content from a sample from the subject, wherein the protease is selected from the group consisting of neutrophil elastase (NE), cathepsin G (CG), proteinase 3 (PR3), and neutrophil secreted protein 4 (NSP4);
   (b) comparing the level of NET-associated protease content with that of a comparable sample from a healthy subject;
   (c) identifying the subject as having a NETosis-related inflammatory condition when the level of the NET-associated protease content of the sample is greater than that of the comparable sample from the healthy subject; and
   (d) treating the NETosis-related inflammatory condition comprising administering to the subject a protease inhibitor, wherein the protease inhibitor inhibits cleavage of peptide substrate comprising a sequence selected from the group consisting of SEQ ID NOs. 1-180.

2. The method of claim 1, wherein the sample is a blood sample.

3. The method of claim 1, wherein the inflammatory condition is selected from the group consisting of infection, systemic lupus erythematosus, rheumatoid arthritis, cystic fibrosis, deep vein thrombosis, pre-eclampsia, periodontitis, appendicitis, tuberculosis, and Crohn's disease.

4. The method of claim 1, wherein treating comprises further administering to the subject a steroid or non-steroidal anti-inflammatory drug.

5. The method of claim 1, wherein treating comprises further administering to the subject an antibiotic.

6. The method of claim 1, wherein obtaining information comprises obtaining a sample from the subject.

7. The method of claim 1, wherein obtaining information comprises performing protease content measurement on the sample.

8. The method of claim 7, wherein the protease content assessment is determined by enzyme-linked immunosorbent assay (ELISA), mass spectrometry, chromatography, electrophoresis, radioimmunoas say, flow cytometry, fluorescence activated cell sorting (FACS), or western blotting.

9. The method of claim 8, wherein the protease content difference between the sample and the comparable sample is +10%, +20%, +25%, +30%, +40%, +50%, +75% or +100%.

10. The method of claim 1, wherein the subject is a human.

11. The method of claim 1, wherein the subject is a non-human mammal.

* * * * *

```
                        SEQUENCE LISTING

<160> NUMBER OF SEQ ID NOS: 180

<210> SEQ ID NO 1
  <211> LENGTH: 8
  <212> TYPE: PRT
  <213> ORGANISM: Artificial sequence
  <220> FEATURE:
  <223> OTHER INFORMATION: Synthetic peptide

<400> SEQUENCE: 1

Ala Thr Gly Gly Tyr His Pro Asn
  1               5

<210> SEQ ID NO 2
  <211> LENGTH: 8
  <212> TYPE: PRT
  <213> ORGANISM: Artificial sequence
  <220> FEATURE:
  <223> OTHER INFORMATION: Synthetic peptide

<400> SEQUENCE: 2

Phe Val Lys Ile Ser Thr Thr His
  1               5

<210> SEQ ID NO 3
  <211> LENGTH: 8
  <212> TYPE: PRT
  <213> ORGANISM: Artificial sequence
  <220> FEATURE:
  <223> OTHER INFORMATION: Synthetic peptide
  <220> FEATURE:
  <221> NAME/KEY: misc_feature
  <222> LOCATION: (6)..(8)
  <223> OTHER INFORMATION: Xaa can be any naturally occurring amino acid

<400> SEQUENCE: 3

Ile Asp Trp His His Xaa Xaa Xaa
  1               5

<210> SEQ ID NO 4
  <211> LENGTH: 8
  <212> TYPE: PRT
  <213> ORGANISM: Artificial sequence
  <220> FEATURE:
  <223> OTHER INFORMATION: Synthetic peptide

<400> SEQUENCE: 4

Met Asp Ser Ile Arg His Gln Gly
  1               5

<210> SEQ ID NO 5
  <211> LENGTH: 8
  <212> TYPE: PRT
  <213> ORGANISM: Artificial sequence
  <220> FEATURE:
  <223> OTHER INFORMATION: Synthetic peptide

<400> SEQUENCE: 5

Pro Ala Lys Val Trp Ser Thr Tyr
```

```
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 6

Gln Arg Arg Gly Met Xaa Xaa Xaa
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 7

Xaa Xaa Pro His Trp Gln Arg Val
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 8

Tyr Arg Met Ile Arg Gln Glu Xaa
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 9

Glu Gln Phe Thr Asn Met Tyr Xaa
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic peptide

<400> SEQUENCE: 10
```

```
Gly Gln Met Ile Arg Trp His Phe
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 11

Ile Ser Thr Thr His Trp Xaa Xaa
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 12

Lys Tyr Pro Ile Met Ala Xaa Xaa
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 13

Met Gln Thr Thr Gln Met Xaa Xaa
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

Asn Gln Ile Ile Trp Phe Asp Tyr
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Pro His Met Ile Trp Ala Lys Pro
```

```
1               5
```

<210> SEQ ID NO 16
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 16

```
Gln Ile Asn Gln Lys His Xaa Xaa
1               5
```

<210> SEQ ID NO 17
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 17

```
Arg Leu Asn Thr Pro Xaa Xaa Xaa
1               5
```

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

```
Arg Met His Val Gln Leu Gly Gly
1               5
```

<210> SEQ ID NO 19
<211> LENGTH: 8
<212> TYPE: PRT
<213> ORGANISM: Artificial sequence
<220> FEATURE:
<223> OTHER INFORMATION: Synthetic peptide

<400> SEQUENCE: 19

```
Ser Glu Thr Ile Ala His Phe His
1               5
```

<210> SEQ ID NO 20
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 20

```
Tyr Asp Pro Val Ser Leu Xaa Xaa
1               5
```

```
<210> SEQ ID NO 21
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 21

Tyr Leu Ala Ile Gln Ala Val Xaa
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 22

Glu Pro Asn Gly Trp Xaa Xaa Xaa
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 23

Gly Arg Asp Thr Met Phe Ile Xaa
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 24

Asn Phe Leu Arg Gly Pro Xaa Xaa
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid
```

```
<400> SEQUENCE: 25

Ala His Trp Val Gly Ile Xaa Xaa
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 26

Ala Ile Gly Ala Arg Ser Asp Xaa
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 27

Lys Ile Ser Thr Thr His Trp Xaa
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 28

Met Ile Trp Ala Lys Pro Gly Xaa
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic peptide

<400> SEQUENCE: 29

Met Val Leu Thr Lys Ala Ala Pro
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic peptide

<400> SEQUENCE: 30
```

```
Thr Val Tyr Ala Asp Ser Ser Glu
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 31

Xaa Xaa Gly Pro Lys Leu Thr Tyr
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 32

Xaa Xaa Xaa Met Pro Glu Glu Val
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 33

Ala Asn Phe Leu Arg Gly Pro Xaa
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 34

Ala Gln Tyr Met Met Gly Gln Xaa
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (8)..(8)
<223> OTHER INFORMATION: Xaa can be any naturally occurring amino acid

<400> SEQUENCE: 35

Ala Val Met Phe Met Ser Lys Xaa
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 36

Asp His Ala Tyr Leu Tyr Xaa Xaa
1               5

<210> SEQ ID NO 37
<211> LENGTH: 8
<212> TYPE: PRT
<213> ORGANISM: Artificial sequence
<220> FEATURE:
<223> OTHER INFORMATION: Synthetic peptide

<400> SEQUENCE: 37

Glu Gln Thr His Asn Tyr Arg Pro
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 38

Glu Arg Leu Phe Phe Trp Ala Xaa
1               5

<210> SEQ ID NO 39
<211> LENGTH: 8
<212> TYPE: PRT
<213> ORGANISM: Artificial sequence
<220> FEATURE:
<223> OTHER INFORMATION: Synthetic peptide

<400> SEQUENCE: 39

Glu Thr Val Tyr Ala Asp Ser Ser
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic peptide

<400> SEQUENCE: 40
```

Gly His Thr Phe Gln Glu Ser Met
1               5

<210> SEQ ID NO 41
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 41

Gly Met Ser Phe Met Met Xaa Xaa
1               5

<210> SEQ ID NO 42
<211> LENGTH: 8
<212> TYPE: PRT
<213> ORGANISM: Artificial sequence
<220> FEATURE:
<223> OTHER INFORMATION: Synthetic peptide

<400> SEQUENCE: 42

His Ala Trp Phe Ser Val Ile Ile
1               5

<210> SEQ ID NO 43
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 43

His Glu Ile Tyr Gly Asp Pro Xaa
1               5

<210> SEQ ID NO 44
<211> LENGTH: 8
<212> TYPE: PRT
<213> ORGANISM: Artificial sequence
<220> FEATURE:
<223> OTHER INFORMATION: Synthetic peptide

<400> SEQUENCE: 44

Ile Ala His Phe His Gly Ile Asp
1               5

<210> SEQ ID NO 45
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 45

Ile Phe Tyr Leu Asn Gly Asp Xaa

<210> SEQ ID NO 46
<211> LENGTH: 8
<212> TYPE: PRT
<213> ORGANISM: Artificial sequence
<220> FEATURE:
<223> OTHER INFORMATION: Synthetic peptide

<400> SEQUENCE: 46

Lys Glu Arg Leu Phe Phe Trp Ala
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47

Lys Leu Thr Tyr Asp Phe Trp Ile
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic peptide

<400> SEQUENCE: 48

Lys Val Asn Phe Gln Gln His Ile
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic peptide

<400> SEQUENCE: 49

Asn Met Leu Lys Asp Asp Met Gly
1               5

<210> SEQ ID NO 50
<211> LENGTH: 8
<212> TYPE: PRT
<213> ORGANISM: Artificial sequence
<220> FEATURE:
<223> OTHER INFORMATION: Synthetic peptide

<400> SEQUENCE: 50

Pro Asp Phe Tyr Leu Gly Arg Ser
1               5

<210> SEQ ID NO 51
<211> LENGTH: 8
<212> TYPE: PRT
<213> ORGANISM: Artificial sequence
<220> FEATURE:
<223> OTHER INFORMATION: Synthetic peptide

<400> SEQUENCE: 51

Arg Ser Ala Phe Ala Glu Met Trp
1               5

```
<210> SEQ ID NO 52
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 52

Arg Trp His Phe Ser Glu Asn Xaa
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic peptide

<400> SEQUENCE: 53

Ser Glu Gln Phe Thr Asn Met Tyr
1               5

<210> SEQ ID NO 54
<211> LENGTH: 8
<212> TYPE: PRT
<213> ORGANISM: Artificial sequence
<220> FEATURE:
<223> OTHER INFORMATION: Synthetic peptide

<400> SEQUENCE: 54

Thr Ala Arg Trp Asn Asp Val Asp
1               5

<210> SEQ ID NO 55
<211> LENGTH: 8
<212> TYPE: PRT
<213> ORGANISM: Artificial sequence
<220> FEATURE:
<223> OTHER INFORMATION: Synthetic peptide

<400> SEQUENCE: 55

Thr Trp Met Lys Ile Phe Asn Thr
1               5

<210> SEQ ID NO 56
<211> LENGTH: 8
<212> TYPE: PRT
<213> ORGANISM: Artificial sequence
<220> FEATURE:
<223> OTHER INFORMATION: Synthetic peptide

<400> SEQUENCE: 56

Val Ile Phe Phe Arg Leu Asn Thr
1               5

<210> SEQ ID NO 57
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
```

```
<222> LOCATION: (6)..(8)
<223> OTHER INFORMATION: Xaa can be any naturally occurring amino acid

<400> SEQUENCE: 57

Val Leu Leu Arg Pro Xaa Xaa Xaa
1               5

<210> SEQ ID NO 58
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 58

Trp Asp Glu Ser Asn Gly Ala Xaa
1               5

<210> SEQ ID NO 59
<211> LENGTH: 8
<212> TYPE: PRT
<213> ORGANISM: Artificial sequence
<220> FEATURE:
<223> OTHER INFORMATION: Synthetic peptide

<400> SEQUENCE: 59

Trp Asn Met Leu Lys Asp Asp Met
1               5

<210> SEQ ID NO 60
<211> LENGTH: 8
<212> TYPE: PRT
<213> ORGANISM: Artificial sequence
<220> FEATURE:
<223> OTHER INFORMATION: Synthetic peptide

<400> SEQUENCE: 60

Trp Ser Thr Tyr Ser Trp Val Ala
1               5

<210> SEQ ID NO 61
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 61

Xaa Met Tyr Phe Lys Tyr Ile Trp
1               5

<210> SEQ ID NO 62
<211> LENGTH: 8
<212> TYPE: PRT
<213> ORGANISM: Artificial sequence
<220> FEATURE:
<223> OTHER INFORMATION: Synthetic peptide

<400> SEQUENCE: 62

Tyr Ile Trp Tyr Val Gln Thr Ala
```

```
1               5
```

<210> SEQ ID NO 63
<211> LENGTH: 8
<212> TYPE: PRT
<213> ORGANISM: Artificial sequence
<220> FEATURE:
<223> OTHER INFORMATION: Synthetic peptide

<400> SEQUENCE: 63

```
Tyr Lys Arg Phe Met Ala His Trp
1               5
```

<210> SEQ ID NO 64
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 64

```
Tyr Thr Leu Lys Gly Glu His Xaa
1               5
```

<210> SEQ ID NO 65
<211> LENGTH: 8
<212> TYPE: PRT
<213> ORGANISM: Artificial sequence
<220> FEATURE:
<223> OTHER INFORMATION: Synthetic peptide

<400> SEQUENCE: 65

```
Ala Phe Met Lys Trp His Glu Gly
1               5
```

<210> SEQ ID NO 66
<211> LENGTH: 8
<212> TYPE: PRT
<213> ORGANISM: Artificial sequence
<220> FEATURE:
<223> OTHER INFORMATION: Synthetic peptide

<400> SEQUENCE: 66

```
Ala Ser Met Arg Ile Tyr Ile Glu
1               5
```

<210> SEQ ID NO 67
<211> LENGTH: 8
<212> TYPE: PRT
<213> ORGANISM: Artificial sequence
<220> FEATURE:
<223> OTHER INFORMATION: Synthetic peptide

<400> SEQUENCE: 67

```
Asp Asp Leu Met Ser Glu Gln Phe
1               5
```

<210> SEQ ID NO 68
<211> LENGTH: 8
<212> TYPE: PRT
<213> ORGANISM: Artificial sequence
<220> FEATURE:
<223> OTHER INFORMATION: Synthetic peptide
<220> FEATURE:

```
<221> NAME/KEY: misc_feature
<222> LOCATION: (6)..(8)
<223> OTHER INFORMATION: Xaa can be any naturally occurring amino acid

<400> SEQUENCE: 68

Asp Thr Met Phe Ile Xaa Xaa Xaa
1               5

<210> SEQ ID NO 69
<211> LENGTH: 8
<212> TYPE: PRT
<213> ORGANISM: Artificial sequence
<220> FEATURE:
<223> OTHER INFORMATION: Synthetic peptide

<400> SEQUENCE: 69

Asp Trp Ala Phe Arg Ile Arg Ser
1               5

<210> SEQ ID NO 70
<211> LENGTH: 8
<212> TYPE: PRT
<213> ORGANISM: Artificial sequence
<220> FEATURE:
<223> OTHER INFORMATION: Synthetic peptide

<400> SEQUENCE: 70

Phe Ile Val Phe Ile Leu Trp Arg
1               5

<210> SEQ ID NO 71
<211> LENGTH: 8
<212> TYPE: PRT
<213> ORGANISM: Artificial sequence
<220> FEATURE:
<223> OTHER INFORMATION: Synthetic peptide

<400> SEQUENCE: 71

Phe Asn Met Tyr Gly Tyr Asp Leu
1               5

<210> SEQ ID NO 72
<211> LENGTH: 8
<212> TYPE: PRT
<213> ORGANISM: Artificial sequence
<220> FEATURE:
<223> OTHER INFORMATION: Synthetic peptide

<400> SEQUENCE: 72

Gly Ile Phe Tyr Leu Asn Gly Asp
1               5

<210> SEQ ID NO 73
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 73

His Ile Val Lys Trp Ala Ser Xaa
1               5
```

```
<210> SEQ ID NO 74
<211> LENGTH: 8
<212> TYPE: PRT
<213> ORGANISM: Artificial sequence
<220> FEATURE:
<223> OTHER INFORMATION: Synthetic peptide

<400> SEQUENCE: 74

Ile Ile Trp Phe Asp Tyr Thr Leu
1               5

<210> SEQ ID NO 75
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 75

Ile Val Lys Trp Ala Ser Xaa Xaa
1               5

<210> SEQ ID NO 76
<211> LENGTH: 8
<212> TYPE: PRT
<213> ORGANISM: Artificial sequence
<220> FEATURE:
<223> OTHER INFORMATION: Synthetic peptide

<400> SEQUENCE: 76

Lys Gly Lys Pro Thr Arg Trp Gln
1               5

<210> SEQ ID NO 77
<211> LENGTH: 8
<212> TYPE: PRT
<213> ORGANISM: Artificial sequence
<220> FEATURE:
<223> OTHER INFORMATION: Synthetic peptide

<400> SEQUENCE: 77

Lys Pro His Asp Val Met Gly Ser
1               5

<210> SEQ ID NO 78
<211> LENGTH: 8
<212> TYPE: PRT
<213> ORGANISM: Artificial sequence
<220> FEATURE:
<223> OTHER INFORMATION: Synthetic peptide

<400> SEQUENCE: 78

Lys Arg Phe Met Ala His Trp Val
1               5

<210> SEQ ID NO 79
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid
```

```
<400> SEQUENCE: 79

Lys Trp Ser Tyr Arg Met Xaa Xaa
1               5

<210> SEQ ID NO 80
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 80

Leu His Pro Phe Lys Val His Xaa
1               5

<210> SEQ ID NO 81
<211> LENGTH: 8
<212> TYPE: PRT
<213> ORGANISM: Artificial sequence
<220> FEATURE:
<223> OTHER INFORMATION: Synthetic peptide

<400> SEQUENCE: 81

Met Ala Phe Met Lys Trp His Glu
1               5

<210> SEQ ID NO 82
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 82

Met Ala His Trp Val Gly Ile Xaa
1               5

<210> SEQ ID NO 83
<211> LENGTH: 8
<212> TYPE: PRT
<213> ORGANISM: Artificial sequence
<220> FEATURE:
<223> OTHER INFORMATION: Synthetic peptide

<400> SEQUENCE: 83

Met Phe Val Lys Ile Ser Thr Thr
1               5

<210> SEQ ID NO 84
<211> LENGTH: 8
<212> TYPE: PRT
<213> ORGANISM: Artificial sequence
<220> FEATURE:
<223> OTHER INFORMATION: Synthetic peptide

<400> SEQUENCE: 84

Met Ile Ala Leu Tyr Trp Gly Arg
1               5
```

```
<210> SEQ ID NO 85
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 85

Met Lys Ile Phe Asn Thr Xaa Xaa
1               5

<210> SEQ ID NO 86
<211> LENGTH: 8
<212> TYPE: PRT
<213> ORGANISM: Artificial sequence
<220> FEATURE:
<223> OTHER INFORMATION: Synthetic peptide

<400> SEQUENCE: 86

Pro Trp Thr Met Ala Asn Phe Leu
1               5

<210> SEQ ID NO 87
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 87

Gln Gly Pro Phe Trp Met Leu Xaa
1               5

<210> SEQ ID NO 88
<211> LENGTH: 8
<212> TYPE: PRT
<213> ORGANISM: Artificial sequence
<220> FEATURE:
<223> OTHER INFORMATION: Synthetic peptide

<400> SEQUENCE: 88

Gln Tyr Pro Met Phe Val Lys Ile
1               5

<210> SEQ ID NO 89
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 89

Arg Leu Phe Phe Trp Ala Xaa Xaa
1               5

<210> SEQ ID NO 90
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 90

Ser Thr Tyr Phe His Asp Leu Asn
1               5

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Thr Lys Met His Ala Glu Asn Ile
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic peptide

<400> SEQUENCE: 92

Val Gly Lys Trp Ser Tyr Arg Met
1               5

<210> SEQ ID NO 93
<211> LENGTH: 8
<212> TYPE: PRT
<213> ORGANISM: Artificial sequence
<220> FEATURE:
<223> OTHER INFORMATION: Synthetic peptide

<400> SEQUENCE: 93

Val Leu Thr Lys Ala Ala Pro Val
1               5

<210> SEQ ID NO 94
<211> LENGTH: 8
<212> TYPE: PRT
<213> ORGANISM: Artificial sequence
<220> FEATURE:
<223> OTHER INFORMATION: Synthetic peptide

<400> SEQUENCE: 94

Trp Leu Ile Phe Val Ser Asn Ala
1               5

<210> SEQ ID NO 95
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 95

Xaa Xaa His Gly Thr Pro Lys Phe
1               5
```

```
<210> SEQ ID NO 96
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 96

Xaa Xaa Leu Phe Asn Asp Val Asn
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Tyr Asn Met Trp Ser Leu Tyr Arg
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 98

Lys Gln Arg Phe His Pro Xaa Xaa
1               5

<210> SEQ ID NO 99
<211> LENGTH: 8
<212> TYPE: PRT
<213> ORGANISM: Artificial sequence
<220> FEATURE:
<223> OTHER INFORMATION: Synthetic peptide

<400> SEQUENCE: 99

Trp Gln Arg Val Ile Phe Phe Arg
1               5

<210> SEQ ID NO 100
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 100

Ile Arg Ser Gly Thr Xaa Xaa Xaa
1               5
```

```
<210> SEQ ID NO 101
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 101

Pro Phe Lys Val His Xaa Xaa Xaa
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 102

Xaa Xaa Xaa Pro Asn Ile Thr Arg
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Arg Phe Met Ala His Trp Val Gly
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Ser Leu Ile Ala Lys Trp Val Gly
1               5

<210> SEQ ID NO 105
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 105

Ser Arg Gln Ala Glu Xaa Xaa Xaa
1               5

<210> SEQ ID NO 106
<211> LENGTH: 8
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 106

Thr Asp Trp Trp Ala Tyr Xaa Xaa
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 107

Xaa Xaa Xaa Ala Gln Asn Glu Ala
1               5

<210> SEQ ID NO 108
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 108

Xaa Xaa Xaa Glu Ala Trp Met Thr
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 109

Leu Gln His Thr Phe Xaa Xaa Xaa
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic peptide

<400> SEQUENCE: 110

Gly Lys Pro Thr Arg Trp Gln Arg
1               5
```

```
<210> SEQ ID NO 111
<211> LENGTH: 8
<212> TYPE: PRT
<213> ORGANISM: Artificial sequence
<220> FEATURE:
<223> OTHER INFORMATION: Synthetic peptide

<400> SEQUENCE: 111

Arg Trp Leu Ile Phe Val Ser Asn
1               5

<210> SEQ ID NO 112
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 112

Trp Val Ala Arg Gly Xaa Xaa Xaa
1               5

<210> SEQ ID NO 113
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 113

Leu Ile Phe Val Ser Asn Ala Xaa
1               5

<210> SEQ ID NO 114
<211> LENGTH: 8
<212> TYPE: PRT
<213> ORGANISM: Artificial sequence
<220> FEATURE:
<223> OTHER INFORMATION: Synthetic peptide

<400> SEQUENCE: 114

Ala Phe Arg Ile Arg Ser Gly Thr
1               5

<210> SEQ ID NO 115
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 115

Glu His His Ala Met Xaa Xaa Xaa
1               5

<210> SEQ ID NO 116
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 116

Phe His Ile Val Lys Trp Ala Ser
1               5

<210> SEQ ID NO 117
<211> LENGTH: 8
<212> TYPE: PRT
<213> ORGANISM: Artificial sequence
<220> FEATURE:
<223> OTHER INFORMATION: Synthetic peptide

<400> SEQUENCE: 117

Phe Val Lys Ile Ser Thr Thr His
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Gly Glu Ala Val Met Phe Met Ser
1               5

<210> SEQ ID NO 119
<211> LENGTH: 8
<212> TYPE: PRT
<213> ORGANISM: Artificial sequence
<220> FEATURE:
<223> OTHER INFORMATION: Synthetic peptide

<400> SEQUENCE: 119

His Gly Phe Glu Tyr Val Thr Ala
1               5

<210> SEQ ID NO 120
<211> LENGTH: 8
<212> TYPE: PRT
<213> ORGANISM: Artificial sequence
<220> FEATURE:
<223> OTHER INFORMATION: Synthetic peptide

<400> SEQUENCE: 120

Lys Phe Gly Ile Phe Tyr Leu Asn
1               5

<210> SEQ ID NO 121
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 121

Leu Ile Ser Val Met Arg Xaa Xaa
1               5
```

```
<210> SEQ ID NO 122
<211> LENGTH: 8
<212> TYPE: PRT
<213> ORGANISM: Artificial sequence
<220> FEATURE:
<223> OTHER INFORMATION: Synthetic peptide

<400> SEQUENCE: 122

Leu Tyr Arg Met Ile Arg Gln Glu
1               5

<210> SEQ ID NO 123
<211> LENGTH: 8
<212> TYPE: PRT
<213> ORGANISM: Artificial sequence
<220> FEATURE:
<223> OTHER INFORMATION: Synthetic peptide

<400> SEQUENCE: 123

Met Glu Phe Ala Thr Gly Gly Tyr
1               5

<210> SEQ ID NO 124
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 124

Met Arg Tyr Ile Asn Val Met Xaa
1               5

<210> SEQ ID NO 125
<211> LENGTH: 8
<212> TYPE: PRT
<213> ORGANISM: Artificial sequence
<220> FEATURE:
<223> OTHER INFORMATION: Synthetic peptide

<400> SEQUENCE: 125

Asn Asn Pro Ile Asp Trp His His
1               5

<210> SEQ ID NO 126
<211> LENGTH: 8
<212> TYPE: PRT
<213> ORGANISM: Artificial sequence
<220> FEATURE:
<223> OTHER INFORMATION: Synthetic peptide

<400> SEQUENCE: 126

Pro Ala Glu Ile Met Gln Thr Thr
1               5

<210> SEQ ID NO 127
<211> LENGTH: 8
<212> TYPE: PRT
<213> ORGANISM: Artificial sequence
<220> FEATURE:
<223> OTHER INFORMATION: Synthetic peptide

<400> SEQUENCE: 127
```

```
Pro Ser Leu Ile Ala Lys Trp Val
1               5

<210> SEQ ID NO 128
<211> LENGTH: 8
<212> TYPE: PRT
<213> ORGANISM: Artificial sequence
<220> FEATURE:
<223> OTHER INFORMATION: Synthetic peptide

<400> SEQUENCE: 128

Ser Gln Thr Ala Arg Trp Asn Asp
1               5

<210> SEQ ID NO 129
<211> LENGTH: 8
<212> TYPE: PRT
<213> ORGANISM: Artificial sequence
<220> FEATURE:
<223> OTHER INFORMATION: Synthetic peptide

<400> SEQUENCE: 129

Trp Glu Arg Thr Ile Val Asn His
1               5

<210> SEQ ID NO 130
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 130

Xaa Ala Met Thr Asp Arg Gly Trp
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 131

Xaa Met Ala Ile His Gly Phe Glu
1               5

<210> SEQ ID NO 132
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 132

Xaa Arg Asp Leu Val Asp His Ile
1               5
```

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133

Tyr Asn Pro Thr Arg Leu His Ser
1               5

<210> SEQ ID NO 134
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 134

Tyr Ser Trp Val Ala Arg Gly Xaa
1               5

<210> SEQ ID NO 135
<211> LENGTH: 8
<212> TYPE: PRT
<213> ORGANISM: Artificial sequence
<220> FEATURE:
<223> OTHER INFORMATION: Synthetic peptide

<400> SEQUENCE: 135

Gly Trp His Ala Met Phe Arg Lys
1               5

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Ile Phe Glu Ile His Gly Val Asp
1               5

<210> SEQ ID NO 137
<211> LENGTH: 8
<212> TYPE: PRT
<213> ORGANISM: Artificial sequence
<220> FEATURE:
<223> OTHER INFORMATION: Synthetic peptide

<400> SEQUENCE: 137

Ile His Asp Val Leu Leu Arg Pro
1               5

<210> SEQ ID NO 138
<211> LENGTH: 8
<212> TYPE: PRT
<213> ORGANISM: Artificial sequence
<220> FEATURE:
<223> OTHER INFORMATION: Synthetic peptide

<400> SEQUENCE: 138

```
Ile Trp Tyr Val Gln Thr Ala Asp
1               5

<210> SEQ ID NO 139
<211> LENGTH: 8
<212> TYPE: PRT
<213> ORGANISM: Artificial sequence
<220> FEATURE:
<223> OTHER INFORMATION: Synthetic peptide

<400> SEQUENCE: 139

Leu Phe Asn Ala Met Thr Trp Pro
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 140

Met Leu Lys Asp Asp Met Gly Xaa
1               5

<210> SEQ ID NO 141
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 141

Asn Pro Thr Arg Leu His Ser Xaa
1               5

<210> SEQ ID NO 142
<211> LENGTH: 8
<212> TYPE: PRT
<213> ORGANISM: Artificial sequence
<220> FEATURE:
<223> OTHER INFORMATION: Synthetic peptide

<400> SEQUENCE: 142

Pro His Asp Val Met Gly Ser Arg
1               5

<210> SEQ ID NO 143
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 143

Gln Asn Lys His Ala Xaa Xaa Xaa
```

```
<210> SEQ ID NO 144
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 144

Ser Trp Val Ala Arg Gly Xaa Xaa
1               5

<210> SEQ ID NO 145
<211> LENGTH: 8
<212> TYPE: PRT
<213> ORGANISM: Artificial sequence
<220> FEATURE:
<223> OTHER INFORMATION: Synthetic peptide

<400> SEQUENCE: 145

Thr His Asn Ala Gly Met Ser Phe
1               5

<210> SEQ ID NO 146
<211> LENGTH: 8
<212> TYPE: PRT
<213> ORGANISM: Artificial sequence
<220> FEATURE:
<223> OTHER INFORMATION: Synthetic peptide

<400> SEQUENCE: 146

Trp Leu Asn Thr Ser Arg Gln Ala
1               5

<210> SEQ ID NO 147
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 147

Trp Asn Asp Val Asp Gly Gly Xaa
1               5

<210> SEQ ID NO 148
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 148

Xaa Xaa Asp Gly Ile Tyr Arg Met
1               5
```

<210> SEQ ID NO 149
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 149

Xaa Xaa Xaa Gly Ala Ser Thr Ser
1               5

<210> SEQ ID NO 150
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 150

Xaa Xaa Xaa Asn His Gln Leu Ala
1               5

<210> SEQ ID NO 151
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 151

Xaa Xaa Xaa Tyr Glu Gln Thr His
1               5

<210> SEQ ID NO 152
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 152

Tyr Ala Asp Ser Ser Glu Trp Xaa
1               5

<210> SEQ ID NO 153
<211> LENGTH: 8
<212> TYPE: PRT
<213> ORGANISM: Artificial sequence
<220> FEATURE:
<223> OTHER INFORMATION: Synthetic peptide

<400> SEQUENCE: 153

Ala Met Met Lys Ile Gly Glu Val

```
1               5

<210> SEQ ID NO 154
<211> LENGTH: 8
<212> TYPE: PRT
<213> ORGANISM: Artificial sequence
<220> FEATURE:
<223> OTHER INFORMATION: Synthetic peptide

<400> SEQUENCE: 154

Ala Met Phe Arg Lys Tyr Pro Ile
1               5

<210> SEQ ID NO 155
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 155

Asp Gln Val Arg Arg Met Asn Xaa
1               5

<210> SEQ ID NO 156
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 156

Asp Ser Ser Glu Trp Xaa Xaa Xaa
1               5

<210> SEQ ID NO 157
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 157

Phe Arg Ile Arg Ser Gly Thr Xaa
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158

Phe Thr Gln Arg Ala Gly Ile Leu
1               5
```

<210> SEQ ID NO 159
<211> LENGTH: 8
<212> TYPE: PRT
<213> ORGANISM: Artificial sequence
<220> FEATURE:
<223> OTHER INFORMATION: Synthetic peptide

<400> SEQUENCE: 159

Gly Glu Asp Arg Asn Thr Phe Tyr
1               5

<210> SEQ ID NO 160
<211> LENGTH: 8
<212> TYPE: PRT
<213> ORGANISM: Artificial sequence
<220> FEATURE:
<223> OTHER INFORMATION: Synthetic peptide

<400> SEQUENCE: 160

Gly Ile Tyr Arg Met His Val Gln
1               5

<210> SEQ ID NO 161
<211> LENGTH: 8
<212> TYPE: PRT
<213> ORGANISM: Artificial sequence
<220> FEATURE:
<223> OTHER INFORMATION: Synthetic peptide

<400> SEQUENCE: 161

Met Phe Leu Arg Glu Lys Gln Tyr
1               5

<210> SEQ ID NO 162
<211> LENGTH: 8
<212> TYPE: PRT
<213> ORGANISM: Artificial sequence
<220> FEATURE:
<223> OTHER INFORMATION: Synthetic peptide

<400> SEQUENCE: 162

Pro Val Ser Arg Gly Leu Tyr Phe
1               5

<210> SEQ ID NO 163
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Xaa can be any naturally occurring amino acid

<400> SEQUENCE: 163

Ser Thr Thr His Trp Xaa Xaa Xaa
1               5

<210> SEQ ID NO 164
<211> LENGTH: 8
<212> TYPE: PRT
<213> ORGANISM: Artificial sequence
<220> FEATURE:
<223> OTHER INFORMATION: Synthetic peptide

<400> SEQUENCE: 164

Ser Tyr Glu Lys Gln Arg Phe His
1               5

<210> SEQ ID NO 165
<211> LENGTH: 8
<212> TYPE: PRT
<213> ORGANISM: Artificial sequence
<220> FEATURE:
<223> OTHER INFORMATION: Synthetic peptide

<400> SEQUENCE: 165

Thr Ala Phe Arg Ser Arg Tyr His
1               5

<210> SEQ ID NO 166
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 166

Xaa His His Phe Thr Gln Arg Ala
1               5

<210> SEQ ID NO 167
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 167

Xaa Pro Ser Phe Asn Met Tyr Gly
1               5

<210> SEQ ID NO 168
<211> LENGTH: 8
<212> TYPE: PRT
<213> ORGANISM: Artificial sequence
<220> FEATURE:
<223> OTHER INFORMATION: Synthetic peptide

<400> SEQUENCE: 168

Ala Gln Leu Arg Ile Gln Asn Arg
1               5

<210> SEQ ID NO 169
<211> LENGTH: 8
<212> TYPE: PRT
<213> ORGANISM: Artificial sequence
<220> FEATURE:
<223> OTHER INFORMATION: Synthetic peptide

<400> SEQUENCE: 169

Ser Leu Tyr Arg Met Ile Arg Gln
1               5

<210> SEQ ID NO 170
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 170

Phe Gln Glu Ser Met Leu Asp Ile
1               5

<210> SEQ ID NO 171
<211> LENGTH: 8
<212> TYPE: PRT
<213> ORGANISM: Artificial sequence
<220> FEATURE:
<223> OTHER INFORMATION: Synthetic peptide

<400> SEQUENCE: 171

Met Leu Asn Ile His Phe Lys Phe
1               5

<210> SEQ ID NO 172
<211> LENGTH: 8
<212> TYPE: PRT
<213> ORGANISM: Artificial sequence
<220> FEATURE:
<223> OTHER INFORMATION: Synthetic peptide

<400> SEQUENCE: 172

Pro Met Phe Val Lys Ile Ser Thr
1               5

<210> SEQ ID NO 173
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 173

Arg Leu Trp Ile His Lys Xaa Xaa
1               5

<210> SEQ ID NO 174
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 174

Arg Thr Glu His His Ala Met Xaa
1               5

<210> SEQ ID NO 175
<211> LENGTH: 8
<212> TYPE: PRT
<213> ORGANISM: Artificial sequence
<220> FEATURE:
<223> OTHER INFORMATION: Synthetic peptide

<400> SEQUENCE: 175
```

```
Asp Gln Pro Val Ser Arg Gly Leu
1               5
```

```
<210> SEQ ID NO 176
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 176

Phe Lys Pro Thr Gly Pro Met Xaa
1               5
```

```
<210> SEQ ID NO 177
<211> LENGTH: 8
<212> TYPE: PRT
<213> ORGANISM: Artificial sequence
<220> FEATURE:
<223> OTHER INFORMATION: Synthetic peptide

<400> SEQUENCE: 177

Phe Gln Glu Ser Met Leu Asp Ile
1               5
```

```
<210> SEQ ID NO 178
<211> LENGTH: 8
<212> TYPE: PRT
<213> ORGANISM: Artificial sequence
<220> FEATURE:
<223> OTHER INFORMATION: Synthetic peptide

<400> SEQUENCE: 178

Asn Lys Arg Ile Ser Gln Trp Met
1               5
```

```
<210> SEQ ID NO 179
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 179

Arg Thr Ile Val Asn His Xaa Xaa
1               5
```

```
<210> SEQ ID NO 180
<211> LENGTH: 8
<212> TYPE: PRT
<213> ORGANISM: Artificial sequence
<220> FEATURE:
<223> OTHER INFORMATION: Synthetic peptide

<400> SEQUENCE: 180

Pro Leu Gly Lys Gln Val Glu Tyr
1               5
```